United States Patent
Ehrnsperger et al.

(10) Patent No.: US 7,918,839 B2
(45) Date of Patent: Apr. 5, 2011

(54) ABSORBENT ARTICLE INCLUDING BARRIER LEG CUFF STRUCTURE AND AN ELASTICALLY STRETCHABLE SIDE PANEL

(75) Inventors: Bruno Johannes Ehrnsperger, Cincinnati, OH (US); Andrew James Sauer, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 648 days.

(21) Appl. No.: 11/251,421

(22) Filed: Oct. 14, 2005

(65) Prior Publication Data
US 2007/0088309 A1 Apr. 19, 2007

(51) Int. Cl.
*A61F 13/15* (2006.01)
*A61F 13/20* (2006.01)

(52) U.S. Cl. ........ 604/385.101; 604/385.24; 604/385.28

(58) Field of Classification Search ........... 604/385.101, 604/385.24–385.3, 393–396
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,081,301 A | 3/1978 | Buell | |
| 4,253,461 A | 3/1981 | Strickland et al. | |
| 4,381,781 A | 5/1983 | Sciaraffa et al. | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,669,622 A | 6/1987 | Bennett | |
| 4,673,402 A | 6/1987 | Weisman et al. | |
| 4,695,278 A * | 9/1987 | Lawson | 604/385.27 |
| 4,704,116 A * | 11/1987 | Enloe | 604/385.27 |
| 4,743,246 A | 5/1988 | Lawson | |
| 4,747,846 A * | 5/1988 | Boland et al. | 604/385.22 |
| 4,834,735 A | 5/1989 | Alemany et al. | |
| 4,846,815 A | 7/1989 | Scripps | |
| 4,857,067 A | 8/1989 | Wood et al. | |
| 4,888,231 A | 12/1989 | Angstadt | |

(Continued)

FOREIGN PATENT DOCUMENTS

EP 0391476 3/1990

(Continued)

OTHER PUBLICATIONS

U.S. Appl. No. 60/543,785, filed Feb. 11, 2004, Catalan et al.

(Continued)

*Primary Examiner* — Michele Kidwell
(74) *Attorney, Agent, or Firm* — John G. Powell; Matthew P. Fitzpatrick

(57) ABSTRACT

An absorbent article includes a barrier cuff strip extending in a longitudinal direction from the front waist region to the back waist region along the topsheet. The barrier cuff strip has a distal edge attached to the topsheet at a cuff end bond region. The barrier cuff has an outer bond edge spaced longitudinally from an inner bond edge. The disposable absorbent article includes a side panel that extends laterally beyond a side of the chassis and is joined to the chassis at a panel joint region extending between an outer panel joint edge and an inner panel joint edge. The longitudinal distance from the lateral axis to the inner panel joint edge is at least about ¼ of a longitudinal distance from the lateral axis to the inner bond edge of the cuff end bond region.

25 Claims, 12 Drawing Sheets

U.S. PATENT DOCUMENTS

| | | | |
|---|---|---|---|
| 4,892,536 A | 1/1990 | Desmarais et al. | |
| 4,894,060 A | 1/1990 | Nestegard | |
| 4,938,753 A | 7/1990 | Van Gompel et al. | |
| 4,938,757 A * | 7/1990 | Van Gompel et al. | 604/396 |
| 4,940,464 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,990,147 A | 2/1991 | Freeland | |
| 5,021,051 A | 6/1991 | Hiuke | |
| 5,026,364 A * | 6/1991 | Robertson | 604/385.3 |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,316 A | 3/1995 | Lavon et al. | |
| 5,397,318 A | 3/1995 | Dreier | |
| 5,496,428 A * | 3/1996 | Sageser et al. | 156/73.1 |
| 5,499,978 A | 3/1996 | Buell et al. | |
| 5,507,736 A | 4/1996 | Clear et al. | |
| 5,514,121 A | 5/1996 | Roe et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,582,606 A * | 12/1996 | Bruemmer et al. | 604/385.28 |
| 5,591,152 A | 1/1997 | Buell et al. | |
| 5,625,222 A | 4/1997 | Yoneda et al. | |
| 5,649,919 A * | 7/1997 | Roessler et al. | 604/385.29 |
| 5,653,703 A | 8/1997 | Roe et al. | |
| 5,685,873 A | 11/1997 | Bruemmer | |
| 5,865,823 A | 2/1999 | Curro | |
| 5,873,870 A | 2/1999 | Seitz et al. | |
| 5,895,382 A * | 4/1999 | Popp et al. | 604/385.21 |
| 5,897,545 A | 4/1999 | Kline et al. | |
| 5,904,673 A | 5/1999 | Roe et al. | |
| 5,931,827 A | 8/1999 | Buell et al. | |
| 5,941,864 A | 8/1999 | Roe | |
| 5,957,908 A | 9/1999 | Kline et al. | |
| 5,977,430 A | 11/1999 | Roe et al. | |
| 5,993,433 A * | 11/1999 | St. Louis et al. | 604/385.27 |
| 5,997,520 A | 12/1999 | Ahr et al. | |
| 6,004,306 A | 12/1999 | Robles et al. | |
| 6,010,491 A | 1/2000 | Roe et al. | |
| 6,013,063 A | 1/2000 | Roe et al. | |
| 6,107,537 A | 8/2000 | Elder et al. | |
| 6,120,487 A | 9/2000 | Ashton | |
| 6,120,489 A | 9/2000 | Johnson et al. | |
| 6,156,024 A * | 12/2000 | Schulte et al. | 604/385.28 |
| 6,159,191 A * | 12/2000 | Mishima et al. | 604/385.28 |
| 6,264,642 B1 * | 7/2001 | Kuen et al. | 604/385.28 |
| 6,432,098 B1 | 8/2002 | Kline et al. | |
| 6,503,237 B1 * | 1/2003 | Lehman et al. | 604/385.28 |
| 6,677,258 B2 | 1/2004 | Carroll et al. | |
| 6,682,516 B2 | 1/2004 | Johnston et al. | |
| 2001/0018580 A1 * | 8/2001 | Suzuki et al. | 604/385.28 |
| 2003/0171731 A1 * | 9/2003 | Johnston et al. | 604/385.27 |
| 2003/0233082 A1 | 12/2003 | Kline et al. | |
| 2004/0013852 A1 | 1/2004 | Curro et al. | |
| 2004/0082931 A1 * | 4/2004 | Tani | 604/387 |
| 2004/0092902 A1 | 5/2004 | Hoffman et al. | |
| 2004/0162536 A1 | 8/2004 | Becker et al. | |
| 2006/0041240 A1 | 2/2006 | Erdman | |

FOREIGN PATENT DOCUMENTS

| | | |
|---|---|---|
| EP | 0 677 284 A1 | 10/1995 |
| EP | 0750895 | 6/2002 |
| WO | WO 93/25172 A1 | 12/1993 |
| WO | WO 94/14395 A1 | 7/1994 |
| WO | WO 95/16746 A1 | 6/1995 |
| WO | WO 2005/051263 A1 | 6/2005 |

OTHER PUBLICATIONS

International Search Report.

* cited by examiner

ABSORBENT ARTICLE INCLUDING BARRIER LEG CUFF STRUCTURE AND AN ELASTICALLY STRETCHABLE SIDE PANEL

FIELD OF INVENTION

The present application relates to absorbent articles and more particularly to an absorbent article including a barrier leg cuff structure and an elastically stretchable side panel.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide or slip down on the body of the wearer during wear. This sagging or gapping and sliding or slipping is caused by the relative motions of the wearer as the wearer breathes, moves, bends and changes positions, by the downward forces generated especially when the absorbent article is loaded with body exudates, and by the deformation of the materials of the absorbent article itself when subjected to such wearer's motions. This sagging or gapping and sliding or slipping of the absorbent article can lead to premature leakage and poor fit of the absorbent article about the wearer in the waist regions and the leg regions of the absorbent article.

In order to more snugly fit absorbent articles about the waist of the wearer, certain commercially available absorbent articles have been provided with elastic waist features. An example of a disposable diaper with an elastic waist feature which has achieved wide acceptance and commercial success is disclosed in U.S. Pat. No. 4,515,595 issued to Kievit and Osterhage on May 7, 1985. Elastic waist features will typically include an elasticized waistband consisting of an elastic member contractibly affixed between the topsheet and the backsheet. The elasticized waistband is designed to expand and contract with the wearer's motions and to maintain the fit of the absorbent article about the waist of the wearer during use (i.e., provide sustained dynamic fit).

However, it has been found that absorbent articles having elastic waist features also have a tendency to sag or gap and slide or slip during use. Further, the elastic waist feature has a tendency to rollover or roll-in at the front of the diaper resulting in a lack of fit about the waist of the wearer.

Thus, it would be advantageous to provide an absorbent article having a waist feature that provides better fit, reduced leakage, and wearer comfort. It would further be advantageous to provide an absorbent article which has reduced sagging, gapping, rollover, or roll-in at the waist of the diaper as well as reduced overall sliding or slipping of the absorbent article or the absorbent core on the wearer during use.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
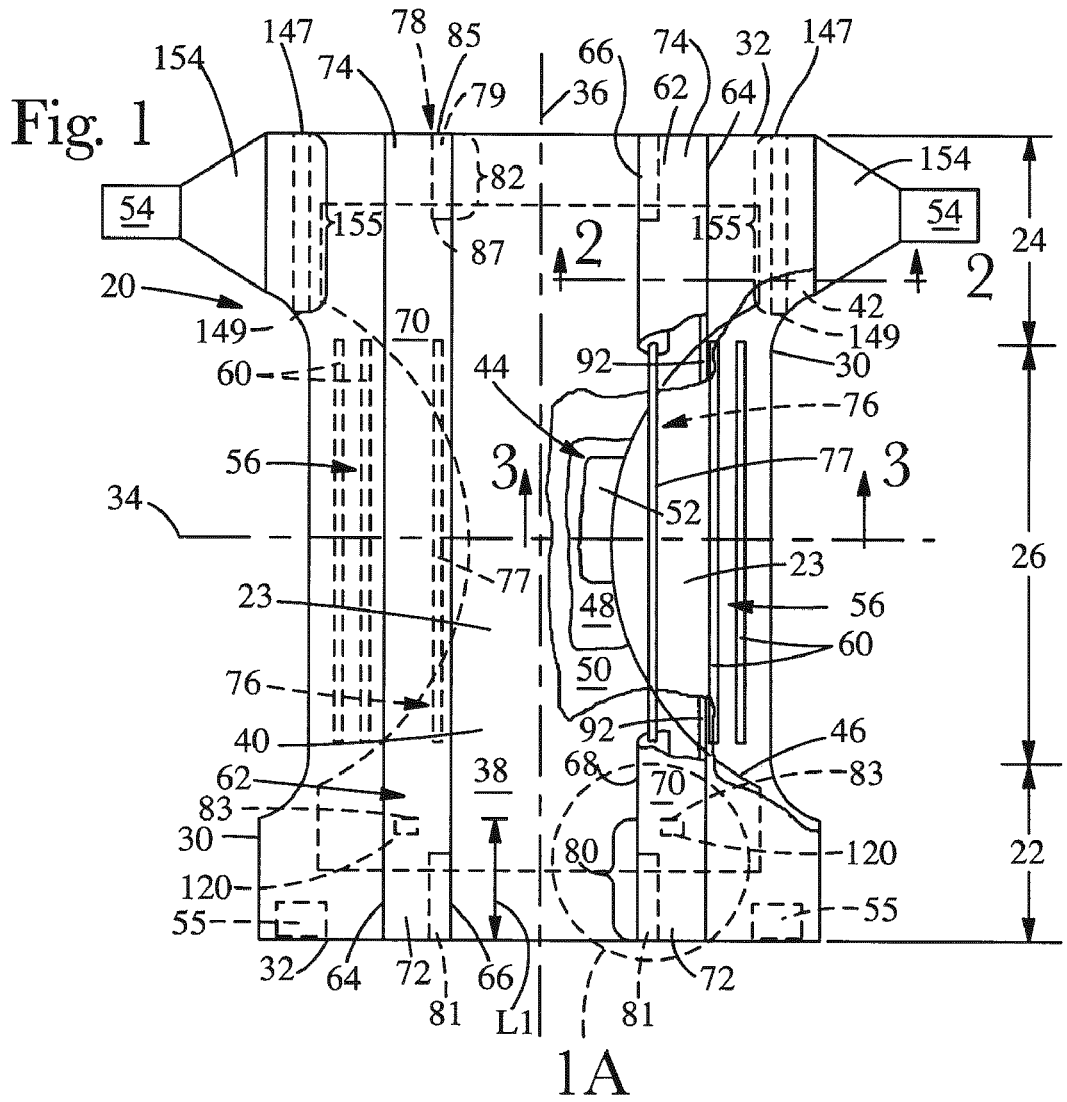
FIG. 1 is a plan view of an absorbent article embodiment having portions cut-away to reveal underlying structure.

All documents cited herein are incorporated herein by reference. The citation of any document is not to be construed as an admission that it is prior art with respect to the present invention.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane" refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. The term "joined" further encompasses configurations where two elements are formed from a single material.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to enter or pass through its thickness in the under typical use conditions (for example without the need to apply a significant or unrepresentative forcing pressure). Conversely, the term "water-impermeable" refers to a layer or a layered structure through the thickness of which liquid water cannot pass in the absence of a forcing pressure (for example, under typical in use conditions). A layer or a layered structure that is water-impermeable according to this definition may be permeable to water vapor, i.e., may be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

As used herein, the term "barrier cuff" refers to an elasticized flap which stands substantially upright, more preferably inwardly towards the longitudinal centerline, within the crotch region. Typically, said barrier cuff envelopes/contains at least one elastic that is connected primarily at its opposing ends to the diaper (e.g., drawstring technique for better fit).

As used herein, the term "gasketing cuff" refers to an elasticized flap which does not stand substantially upright, or which more preferably is disposed outwardly towards the longitudinal side edges of the diaper, within the crotch region. Typically, said gasketing cuff envelopes/contains at least one elastic that is connected substantially throughout its length to the diaper (e.g., multiple bonds along length of elastic to create gathers).

FIG. 1 is a plan view of an exemplary, non-limiting embodiment of a diaper 20 in a flat-out, uncontracted state (i.e., without elastic induced contraction) with portions of the structure being cut away to more clearly show the underlying structure of the diaper 20 and with the portion of the diaper 20 which contacts the wearer facing the viewer. The diaper 20 is shown in FIG. 1 to have a front waist region 22, a back waist region 24, a crotch region 26, and a periphery 28 which is defined by the outer edges of the diaper in which the longitudinal edges are designated 30 and the end edges are designated 32. The diaper 20 additionally has a lateral axis or centerline which is designated 34 and a longitudinal axis or centerline which is designated 36.

A main body or chassis 23 of the diaper 20 has an outer covering including liquid permeable topsheet 38, a top surface of the topsheet 38 being designated 40; a liquid impermeable backsheet 42; and an absorbent core 44 having side edges 46 and comprising an absorbent layer 48 and first and second tissue layers (or nonwoven wrapping layers) 50 and 52, respectively, encased between the topsheet 38 and backsheet 42. For unitary absorbent articles, the chassis 23 comprises the main structure of the diaper with other features added to form the composite diaper structure. For example, the diaper 20 may include a pair of fastener components 54; gasketing cuffs 56 each comprising side flap 58 and flap elastic members 60; barrier cuffs 62 each having a proximal edge 64, a distal edge 66, an inboard surface 68, an outboard surface 70, a first end 72 and a second end 74; and spacing means 76, such as spacing elastic member 77 for spacing the distal edge 66 away from the topsheet top surface 40. The diaper 20 additionally includes a bond 78 and/or multiple bonds 78, 120 such as an adhesive glue bead for securing closed the first and second ends 72 and 74 of each barrier cuff 62. Other attachment means 78 may include thermal bonds, mechanical bonds, pressure bonds, ultrasonic bonds, combinations of these, or the like. The areas in which the bond 78 and, in some embodiments, bond 120 are disposed are designated the front bond region 80 and the back bond region 82. The front bond regions 80 begin at an outer bond edge 81 located at the first end 72 and end at an inner bond edge 83 that is spaced longitudinally from the outer bond edge 81. Similarly, back bond regions 82 begin at an outer bond edge 85 located at the second end 74 and end at an inner bond edge 87 that is spaced longitudinally from the outer bond edge 85. In the illustrated embodiment, the outer bond edges 81, 85 are formed by bonds 78, the inner bond edges 83 are formed by discrete, separate bonds 120 that are spaced longitudinally from the bonds 78 and the inner bond edges 87 are formed by bonds 78. As shown, the bonds 120 and 78 may be offset laterally from each other. Alternatively, the bonds 120, 78 may be substantially laterally aligned.

Figure 1A:
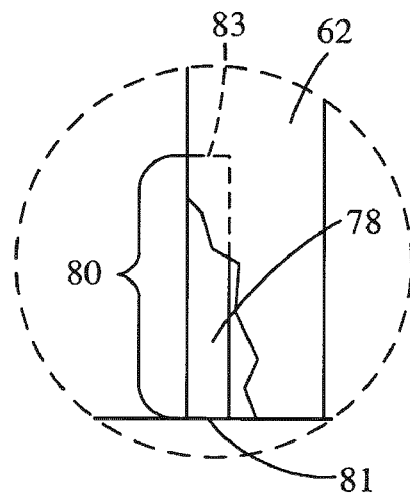
FIG. 1A is a plan view of an embodiment of a bonding pattern forming an end bond region.
Figure 1B:
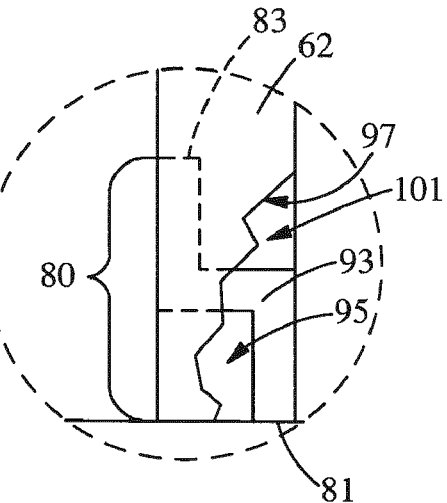
FIG. 1B is a plan view of another embodiment of a bonding pattern forming an end bond region.
Figure 1C:
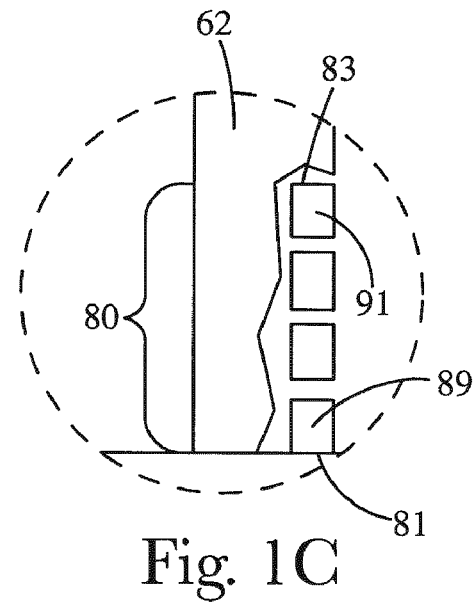
FIG. 1C is a plan view of another embodiment of a bonding pattern forming an end bond region.

Referring to FIG. 1A, any one or more of the bond regions 80, 82 may be formed by a single, continuous bond 78 that extends continuously from an outer bond edge 81, 85 to an inner bond edge 83, 87. FIG. 1B shows another embodiment where a bond region 80, 82 is formed by a continuous bond 93 having a first portion 95, a second portion 97 and a third portion 101 connecting the first and second portions. As can be seen, the first portion 95 is offset laterally from the second portion 97. As another exemplary embodiment, FIG. 1C shows more than two bonds forming the bond region 80, 82 where outermost bond 89 forms outer bond edge 81, 85 and innermost bond 91 forms inner bond edge 83, 87. The terms "outer" and "inner" are relative to the lateral centerline 34.

Referring back to FIG. 1, while the topsheet 38, the backsheet 42, and the absorbent core 44 may be assembled in a variety of well-known configurations, preferred diaper configurations are described generally in U.S. Pat. No. 3,860,003 entitled "Contractible Side Portions for Disposable Diaper"

issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999.

FIG. 1 shows an embodiment of the diaper 20 in which the topsheet 38 and the backsheet 42 are coextensive and have length and width dimensions generally larger than those of the absorbent core 44. The topsheet 38 is associated with and superposed on the backsheet 42 thereby to form the periphery 28 of the diaper 20. The periphery 28 defines the outer perimeter or, in other words, the edges of the diaper 20. The periphery 28 includes the end edges 32 and the longitudinal edges 30. The topsheet 38 need not be generally coextensive with the backsheet 42. For example, the topsheet 38 could be more narrow than the backsheet 42 or more wide than the backsheet 42. The overall diaper structure could be a shaped structure with a narrowing in the crotch region 26 as shown in FIG. 1. "Ear" or side panels 154 are joined to the chassis 23 at the back waist region 24. In some embodiments, such side panels 154 could be integral with the chassis or be separately attached. In some implementations, the side panels 154 may be formed of multiple layers where one or more of the layers is formed by the backsheet 42, the topsheet 38 and/or separately formed layers of material, such as an elastomeric layer. In some embodiments, side panels 154 may extend from the chassis 23 at the front waist region 22, for example, instead of or in addition to at the back waist region 24.

It may be desirable to provide the diaper 20 with extensibility or elasticity in all or a portion of the side panels 154. As used herein, the terms "extensible" and "stretchable" refer to materials that are capable of extending in at least one direction to a certain degree without rupture. The terms "elasticity", "elastically extensible" and "elastically stretchable" refer to extensible materials that have the ability to return to approximately their original dimensions after the force that extended the material is removed. As used herein, any material or element described as extensible or as stretchable may also be elastically extensible or elastically stretchable unless otherwise provided. Extensible side panels 154 may provide a more comfortable and contouring fit by initially conformably fitting the diaper 20 to the wearer and sustaining this fit throughout the time of wear even after the diaper has been loaded with exudates since extensible side panels 154 can allow the sides of the diaper 20 to expand and contract. Extensible side panels 154 may also further provide more effective application of the diaper 20 since even if one pulls one side panel 154 farther than the other side panel 154 during application of the diaper, the diaper may self-adjust during wear. Fasteners, such as fasteners 54 may be attached to or integral with such side panels 154 if they are included.

While the extensible side panels 154 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; in U.S. Pat. No. 5,151,092 issued to Buell et al. on Sep. 29, 1992; U.S. Pat. No. 6,677,258 issued to Carroll et al. on Jan. 13, 2004 and U.S. patent application Ser. No. 10/396,977 filed on Mar. 25, 2003.

Side panels 154 may be joined to the diaper 20 in any suitable manner. Side panels 154 may be affixed directly to the backsheet 42 at a panel joint region 155, e.g., formed by adhesive, pressure bonding or any other attachment material and/or process. As noted above, joining the side panels 154 to the chassis 23 at panel joint region 155 may consist of joining only one or more layers of the side panels, such as joining only an elastomeric layer of the side panels to the chassis. In embodiments where only one or more of multiple layers forming the side panels 154 are separately formed and joined to the chassis 23, the panel joint region 155 is formed at the joint location where the separately formed material (e.g., an elastomeric sheet) is joined to the chassis 23. In some embodiments, the joint region 155 may be formed by more than one process, such as by an adhesive bond and a pressure bond. Certain attachment methods are described in U.S. Pat. No. 6,677,258 already referred to above. Joint region 155 has an outer panel joint edge 147 formed at an outermost bond location between the side panel 154 and the backsheet 42 and an inner panel joint edge 149 formed at an innermost bond location between the side panel 154 and the backsheet 42. Joint region 155 may be formed by several, longitudinally spaced-apart bonds and/or joint region 155 may be formed by a single, continuous bond.

The diaper 20 has front and back waist regions 22 and 24 extending respectively from the end edges 32 of the diaper periphery 28 toward the lateral axis 34 of the diaper 20 a distance from about ¼ to about ⅓ the length of the diaper 20. The waist regions comprise those portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

Figure 2:
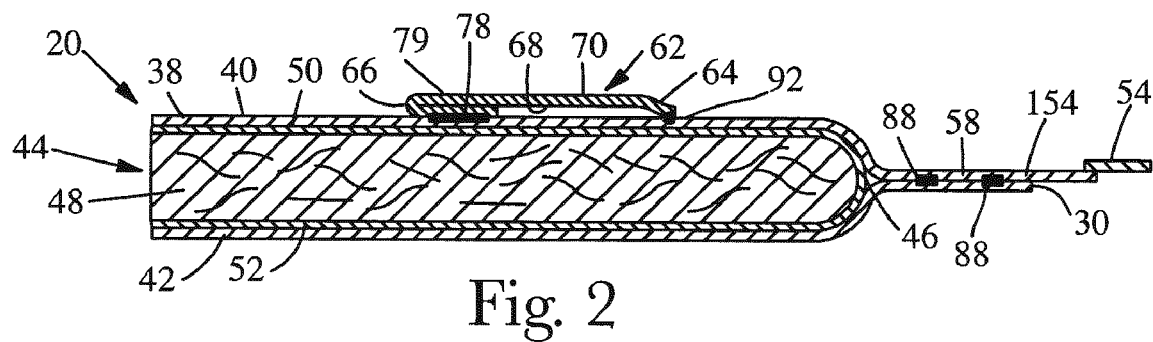
FIG. 2 is a fragmentary sectional view taken along section line 2-2 of FIG. 1.

FIG. 2 is a fragmentary sectional view taken along line 2-2 of FIG. 1 and depicts the diaper construction in the back waist region 24 of the diaper 20. The absorbent core comprises the absorbent layer 48 that is shown as being completely enveloped by the first and second tissue layers (or nonwoven layers) 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together such as by adhesive 88. In the illustrated embodiment, the flap elastic members 60 do not extend into the waist region so that the gasketing cuff 56 is not formed in this region. The barrier cuff 62 is shown as being a separate element secured to the topsheet 38; the proximal edge 64 being formed by securing the element to the topsheet 38 by bond 92. Bond 92 could be any suitable attachment mechanism such as adhesive, mechanical bonding, thermal bonding, pressure bonding, ultrasonic bonding, combinations of these, or the like. The inboard surface 68 of the barrier cuff 62 is secured to the topsheet top surface 50 by bond 78 such as the glue bead 79. This bond 78 could also be accomplished through a variety of mechanisms such as adhesive, mechanical bonding, thermal bonding, pressure bonding, ultrasonic bonding, or the like. Therefore, the distal edge 66 is closed (i.e., it is not spaced away from the topsheet top surface 40). It should be noted that the spacing elastic member 77 is not disposed in this region because the distal edge 66 is not designed to be spaced away from the topsheet top surface 40 in the waist regions. Therefore, the barrier cuff 62 is neither open nor ready to constrain the flow of body exudates in this region.

Figure 3:
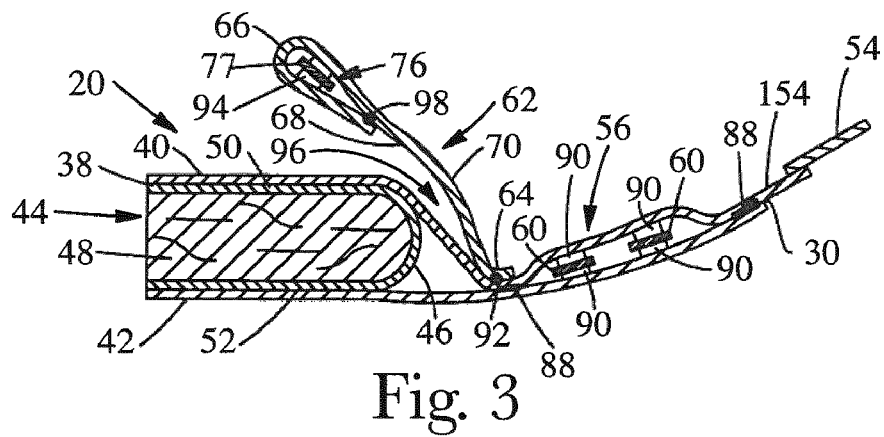
FIG. 3 is a fragmentary sectional view taken along section line 3-3 of FIG. 1.

FIG. 3 is a fragmentary sectional view taken along line 3-3 of FIG. 1 and depicts the diaper construction in the crotch region 26 of the diaper 20 as it is shaped before being applied to the wearer (i.e., the diaper 20 is subjected to elastic contraction). The absorbent core 44 comprises the absorbent layer 48 that is shown as being completely enveloped by the first and second tissue or nonwoven layers 50, 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together by a joint such as an adhesive bond 88. The topsheet 38 and the backsheet 42 also enclose the flap elastic members 60 adjacent the longitudinal edge 30 in the periphery 28. The flap elastic members 60 are secured in the topsheet-backsheet formed side flap 58 by elastic attachment means 90. The elastically contractible gasketing cuff 56 is thereby formed by the side flap 58 by elastic attachment means 90. The barrier cuff 62 is shown as being formed by securing an element to the topsheet 38 between the flap elastic members 60 and the side edge 46 of the absorbent core 44. The proximal edge 64 of the barrier cuff 62 is formed by securing the barrier cuff element to the topsheet 38 by attachment means 92. The spacing elastic members 77 are enclosed in a tunnel that is formed when an end of the barrier cuff element is folded back on itself; the spacing elastic members 77 being secured in the barrier cuff 62 by elastic attachment bond 94, the elastic members 77 being unattached in the crotch region 26 or, alternatively, the elastic members may be attached in the crotch region 26, for example, with an extension of the elastic attachment bond 94, or with a separate bond. The distal edge 66 of the barrier cuff is spaced away from the topsheet top surface 40 by the elastic gathering action of the spacing elastic members 77; a channel 96 thereby being formed by at least the proximal edge 64, the distal edge 66 and the inboard surface 68 of the barrier cuff 62. The channel 96 is shown as being ready to restrain, contain, and hold body exudates until the diaper 20 is removed from the wearer.

The topsheet 38 may be fully or partially elasticized or may be foreshortened so as to provide a void space between the topsheet 38 and the core 44. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets."

The absorbent core 44 may comprise any absorbent material that is generally compressible, conformable, non-irritating to the wearer's skin, and capable of absorbing and retaining liquids such as urine and other certain body exudates. The absorbent core 44 may include first and second opposed faces and comprise an absorbent layer 48 and first and second tissue or nonwoven layers 50, 52. The first and second tissue or nonwoven layers 50, 52 may overlay the major surfaces of the absorbent layer 48 to form the first and second opposed faces of the absorbent core. The absorbent core 44 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 44 may be comprised of multiple layers including a layer or multiple layers forming an acquisition and/or distribution system. Such an acquisition or distribution layer may be coextensive with the remaining layers of the core, or may be or different dimensions or positioning. The absorbent core 44 may be made predominately of superabsorbent material (e.g., about 50 weight percent or more, such as about 60 weight percent or more, such as about 70 weight percent or more, such as about 80 weight percent or more, such as about 90 weight percent) without the addition of absorbent fibers (such as a "airfelt free" core). Such an airfelt free core may comprise predominately superabsorbent particles, and a microfiber glue. Superabsorbent materials are those which are capable of absorbing at least about 10 grams, e.g., at least about 20 grams or more, of Synthetic Urine (0.9 percent NaCl aqueous solution) per gram of superabsorbent material. The core structure may also include wetness sensation members or a combination of wetness sensation member (or members) and an acquisition layer or layers. Any or all of the core structures (such as the optional wetness sensation member(s) or acquisition layer(s)) may be tinted or highlighted for visibility if desired.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997; and U.S. patent application No. 2004/0162536 published on Aug. 19, 2004 entitled "Comfortable Diaper."

The backsheet 42 is generally that portion of the diaper 20 positioned adjacent the garment-facing surface of the absorbent core 44. Backsheet 42 prevents the exudates absorbed and contained therein from soiling articles that may contact the diaper 20, such as bed sheets and undergarments. In preferred embodiments, the backsheet 26 is substantially impermeable to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 42. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and U.S. Pat. No. 5,865,823 issued to Curro on Feb. 2, 1999. Other breathable backsheets including nonwoven webs and apertured formed films are described in U.S. Pat. No. 5,571,096 issued to Dobrin et al. on Nov. 5, 1996. An exemplary, suitable backsheet is disclosed in U.S. Pat. No. 6,107,537 entitled "Disposable absorbent articles providing a skin condition benefit" issued to Elder et al on Aug. 22, 2000. Other suitable materials and/or manufacturing techniques may be used to provide a suitable backsheet 42 including, but not limited to, surface treatments, particular film selections and processing, particular filament selections and processing, etc.

Backsheet 42 may also consist of more than one layer, as exampled in FIG. 1, wherein a backsheet outer layer (often referred to as the backsheet) may be made of a soft, nonwoven material and a backsheet inner layer may be made of a substantially impermeable film. Adhesive or any other suitable material or method may be used to join layers and together. While a variety of backsheet configurations are contemplated herein, it would be obvious to those skilled in the art that various other changes and modifications can be made without departing from the spirit and scope of the invention.

The diaper 20 may also include a flexible fastening system. The fastening system preferably maintains the front waist region 22 and the back waist region 24 in a configuration so as to provide lateral tensions about the circumference of the diaper 20 to hold the diaper 20 on the wearer. Flexible fastening system includes a first fastener component 54 and a second, fastener component 55 capable of releasably mating with the first fastener component 54. The fastener components 54 and 55 such as a base of the fastener components can be formed of a flexible material, e.g., having a flexural modulus of 80 Kpsi or less, such as between about 10 Kpsi and about 80 Kpsi. In some embodiments, the fastener components may be formed of a material having a relatively low modulus of elasticity, such as about 1 Gpa or less, such as about 0.5 Gpa or less.

By forming fastener components 54 and 55 of a relatively flexible material, greater body conformity can be achieved. "Body conformity" refers to the percent deflection of a fastening device in the fastened configuration per force (kgf) of compressive deflection load of a fastening device. The body conformity of a fastening device may be measured with the fastening device in a fastened configuration with the fastener components 54 and 55 of the fastening device interlocked. In some embodiments, it is preferable to have a body conformity of greater than about 500 percent per kilogram force of load (%/kgf), such as greater than about 1000%/kgf. Details of measuring body conformity of a fastening device is described in U.S. patent application No. 2003/0233082, entitled "Highly Flexible And Low Deformation Fastening Device", Published on Dec. 18, 2003.

First fastener component 54 is in the form of tape tabs 54, which may be applied to the back waist region 24 (or front waist region 22) of the diaper 20. Alternatively, the fastening system may employ adhesive fasteners, cohesive fasteners, selective adhesive fasteners, mechanical fasteners, hook and loop fastening components, interlocking fasteners such as tabs & slots, buckles, buttons, snaps, macro-fasteners, and/or hermaphroditic fastening components, and combinations of any of these although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in U.S. Pat. No. 6,432,098 entitled "Absorbent Article Fastening Device" in the names of Kline et al. issued on Aug. 13, 2002. The fastening system 55 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997.

In some embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application No. 2003/0233082, entitled "Highly Flexible And Low Deformation Fastening Device", Published on Dec. 18, 2003; U.S. Pat. No. 5,897,545, issued to Kline et al. on Apr. 27, 1999; U.S. Pat. No. 5,957,908, issued to Kline et al on Sep. 28, 1999.

The diaper 20 may also include such other features as are known in the art including graphics, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092.

In the embodiment illustrated in FIG. 1, each barrier cuff 62 is a flexible member having a proximal edge 64, a distal edge 66, an inboard surface 68, and an outboard surface 70. As used herein, the term flexible refers to materials which are compliant and will readily conform to the general shape and contours of the body. In addition, if the spacing means 76 comprise spacing elastic members 77, the barrier cuff 62 should be contractible so that the distal edge 66 may be sufficiently spaced away from the topsheet top surface 40 so that a channel 96 is formed to restrain, contain, and hold body exudates within the article. The barrier cuff 62 may be manufactured from a wide variety of materials such as polypropylene, polyester, rayon, nylon, foams, plastic films, formed films, and elastic films. The barrier cuff 62 may also include absorbent materials including absorbent glue, if desired. A number of manufacturing techniques may be used to manufacture the barrier cuff. For example, the barrier cuff 62 may be woven, non-woven, spunbonded, carded, or the like.

As shown in FIGS. 1 and 3, the barrier cuff 62, and more particularly the proximal edge 64, is disposed inboard of and preferably adjacent to the gasketing cuff 56. The term "inboard" is defined as the direction toward the centerline (34 or 36, respectively) of the diaper that is parallel to the respective edge of the diaper 20 along which the particular gasketing cuff 56 is disposed. The barrier cuff 62 is disposed inboard of the gasketing cuff 56 so that exudates, especially loose fecal material which is not easily absorbed and tends to float along the topsheet top surface 40, will contact the barrier cuff 62 before it can contact the gasketing cuff 56. The barrier cuff 62 is disposed adjacent the gasketing cuff 56 to provide a more effective dual restraint against the flow of body exudates.

The proximal edge 64 and the distal edge 66 are in spaced relation to each other and define the width of the barrier cuff 62. The proximal and distal edges 64, 66 may be in a parallel, non-parallel, rectilinear, or curvilinear relationship. In addition, the barrier cuff 62 may have a variety of different cross-sectional areas including circular, square, rectangular, or any other shape such as shown in FIG. 3. The proximal edge 64 may be spaced from the distal edge 66 in a parallel and rectilinear relationship to provide a barrier cuff 62 having uniform width. Each barrier cuff 62 may have a width of at least 5 mm and may be approximately 10-50 mm. The barrier cuff 62 may be formed from a folded structure in which portions of the cuff material may be folded back upon itself at one or more locations. In such constructions the distal and proximal edges usually are the most inboard and outboard locations of the cuff material with regard to any folding back of such cuff material.

Each barrier cuff 62 may be joined to the topsheet 38. As noted above, the term joined includes any means for affixing the barrier cuff 62 to the diaper 20, and includes embodiments wherein the barrier cuff 62 is a separate element having a proximal edge 64 directly or indirectly attached to the topsheet 38 or embodiments wherein the barrier cuff 62 is made from the same element or material as the topsheet 38 so that the proximal edge 64 is a continuous and undivided element of the topsheet 42. The barrier cuff 62 may alternatively be joined to the backsheet 42, the absorbent core 44, the topsheet 38, or any combination of these or other elements of the diaper 20. If provided integrally with the topsheet 38, the barrier cuff 62 may be formed by a single strip of material which is secured to the topsheet 38 by attachment means 92, the distal edge 66 being formed by folding an end of the material back upon itself. The barrier cuff 62 can also be formed out of the same material as the topsheet 38 or the backsheet 42 or by the combination of the topsheet and backsheet materials. Additionally, the barrier cuff 62 may be formed out of a portion of the core assembly.

The distal edge 66 may be disposed inboard of the proximal edge 64 to present a more effective barrier against the flow of exudates. The distal edges 66 are maintained inboard of the proximal edges 64 by attachment means 78 (such as adhesive, thermal bonds, pressure bonds, ultrasonic bonds, etc.) so as to obviate their inversion. The distal edge 66 may be unsecured to any other element in at least the crotch region 26 of the diaper 20 so that it may be spaced away from the top surface 40 of the topsheet 38. The distal edge 66 may be spaced from the topsheet top surface 40 so that the barrier cuff 62 may form a channel 96 to enhance containment of the article. As used herein, "spaced" includes embodiments wherein the distal edges 66 may assume one or more positions relative to the topsheet top surface 40 including at some times assuming a position adjacent the topsheet top surface. The distance between the distal edge 66 to the topsheet top surface 40 is measured along a line drawn from the distal edge 66 to the closest part of the topsheet 38 when the distal edge 66 is positioned so as to be spaced away from the topsheet as far as possible (i.e., in the elastically contracted position). The distal edge 66 may be spaced away from the topsheet 38 by a height of at least 2 mm, and more may be spaced from about 5 mm to about 50 mm.

The channel 96 is formed at least along the proximal and distal edges 64, 66 and the inboard surface 68 of the barrier cuff 62. The channel 96 forms a barrier to the flow of exudates as they tend to move or float across the topsheet 38. Thus, the channel 96 holds and contains exudates until the diaper 20 can be removed. The barrier cuffs 62 may be provided with absorbent means and/or may be rendered liquid impermeable as disclosed in U.S. Pat. No. 4,743,246 which issued to Lawson on May 10, 1988.

The spacing means 76 for spacing the distal edge 66 away from the topsheet top surface 40 is any member which gathers, contracts, stiffens, shortens, or otherwise acts on the barrier cuff 62 so as to cause a channel 96 to be formed along the barrier cuff 62 to provide a constraint against the leakage of exudates. As shown in FIG. 1, the spacing means 76 may comprise a spacing elastic member 77 secured adjacent the distal edge 66 inside the barrier cuff 62. The spacing elastic member 77 is preferably secured to the barrier cuff 62 in an elastically contractible condition so that in a normally unrestrained configuration, the spacing elastic member 77 effectively contracts or gathers the barrier cuff 62. The spacing elastic member 77 can be secured to the barrier cuff 62 in an elastically contractible condition in at least two ways as is discussed in the above-referenced U.S. Pat. No. 3,860,003 issued to K. B. Buell. In addition, the length of the spacing elastic member 77 in general is dictated by the diaper design.

In the embodiment illustrated in FIG. 1, the spacing elastic member 77 extends essentially the entire length of the barrier cuff 62 in the crotch region 26, although other lengths are cognizable. Additional details and alternatives for the spacing means are discussed in the above-referenced U.S. Pat. No. 4,743,246 to Lawson.

Bonds 78 for securing end portions 72 and 74 of the barrier cuff 62 closed are shown in FIGS. 1 and 2. The bonds 78 provide a more comfortable fit for the wearer and obviate inversion of the distal edges 66 of the barrier cuff 62 during application and use. Inversion is generally defined as the inboard disposed distal edge 66 turning outwardly when the diaper 20 is applied to the wearer. In the embodiment illustrated at FIGS. 1 and 2, such bonds 78 are disposed in the front waist region 22 and the back waist region 24 of the diaper in the front bond region 80 and the back bond region 82, respectively. The remaining portions of the barrier cuff 62 may not be secured closed so that the distal edges 66 are generally left freely openable.

Figure 4:
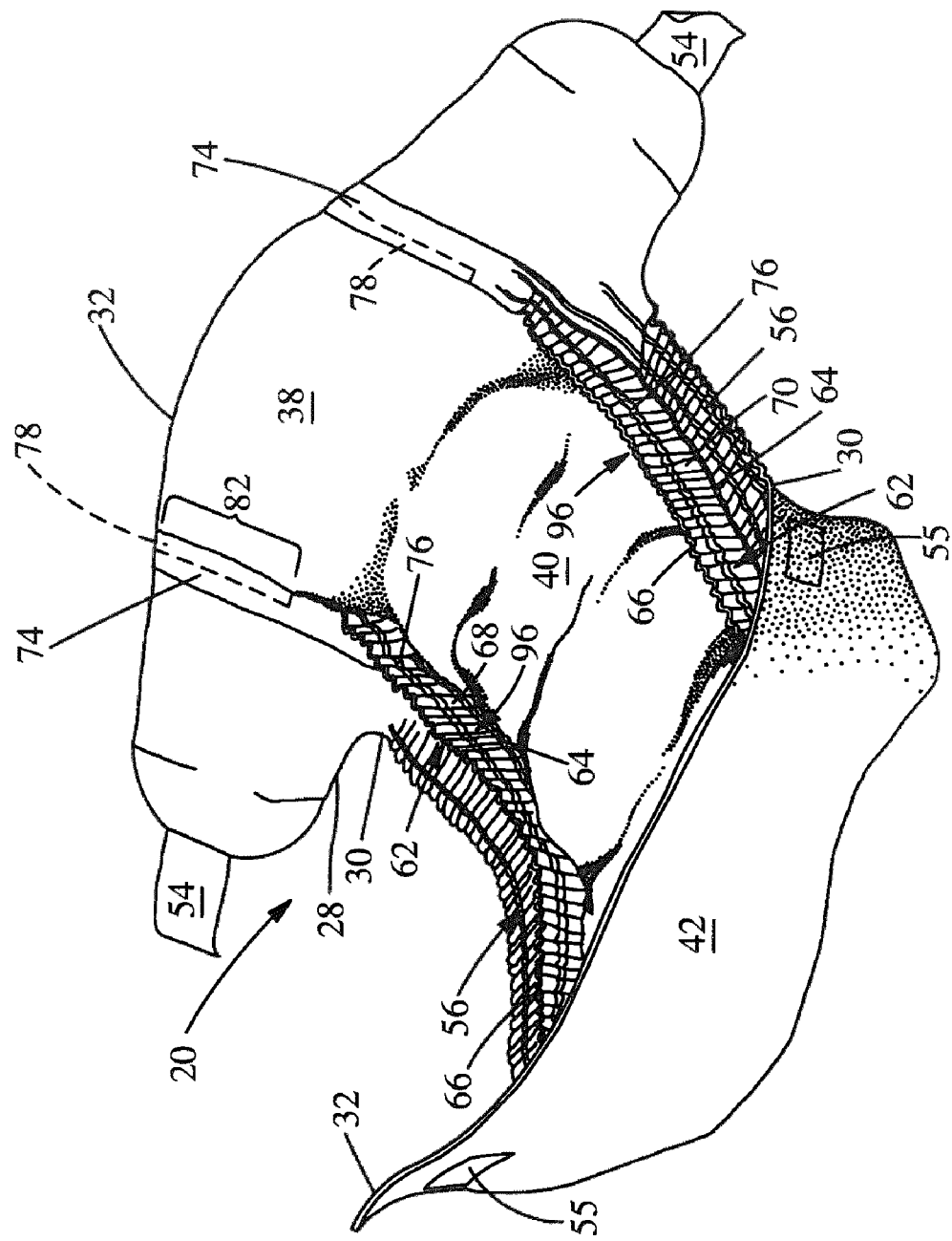
FIG. 4 is a perspective view of the absorbent article embodiment of FIG. 1.

FIG. 4 is a sectional view of the diaper 20 in its elastically contracted position prior to being placed on the wearer. The topsheet 38 is shown as the body contacting surface of the diaper 20, the backsheet 42 being disposed away from the body of the wearer. The gasketing cuffs 56 are shown to be gathered or contracted. The diaper 20 is shown as having two barrier cuffs 62 extending adjacent to and inboard of the gasketing cuffs 56. The distal edges 66 are shown to be gathered and contracted by the spacing elastic members (not shown) in the crotch region 26 so as to provide a longitudinally extending channel 96 along the diaper 20. In addition, the ends 72, 74 of the barrier cuff are secured closed in the front and back bond regions 80, 82, respectively, so as to provide comfort for the wearer, to obviate inversion of the barrier cuffs, and for ease of application of the diaper.

One way of applying the diaper 20 is by positioning the back waist region 24 under the wearer's back, and drawing the remainder of the diaper 20 between the wearer's legs so that the front waist region 22 is positioned across the front of the wearer. The ends of the tape-tab fasteners 54 are then secured to outwardly facing areas 55 (or mating fastener components) of the diaper 20. In this manner the barrier cuffs 62 should be disposed in the crotch region of the wearer and should provide the dispositions and functions described hereinbefore. The diaper 20 may also be applied with the wearer standing up, if desired. Once applied, the distal edges 66 of the barrier cuffs 62 extend through the groin area and diverge upwardly along both of the buttocks of the wearer. Neither of the barrier cuffs 62 encircles the thighs of the wearer. However, the gasketing cuffs 56 will encircle the thighs and create a gasketing action against the thighs. The ends 72, 74 of the barrier cuff 62 are secured to the topsheet 38 to obviate the inversion of the barrier cuffs, for comfort to the wearer during application and use, and for ease of application.

Figure 5:
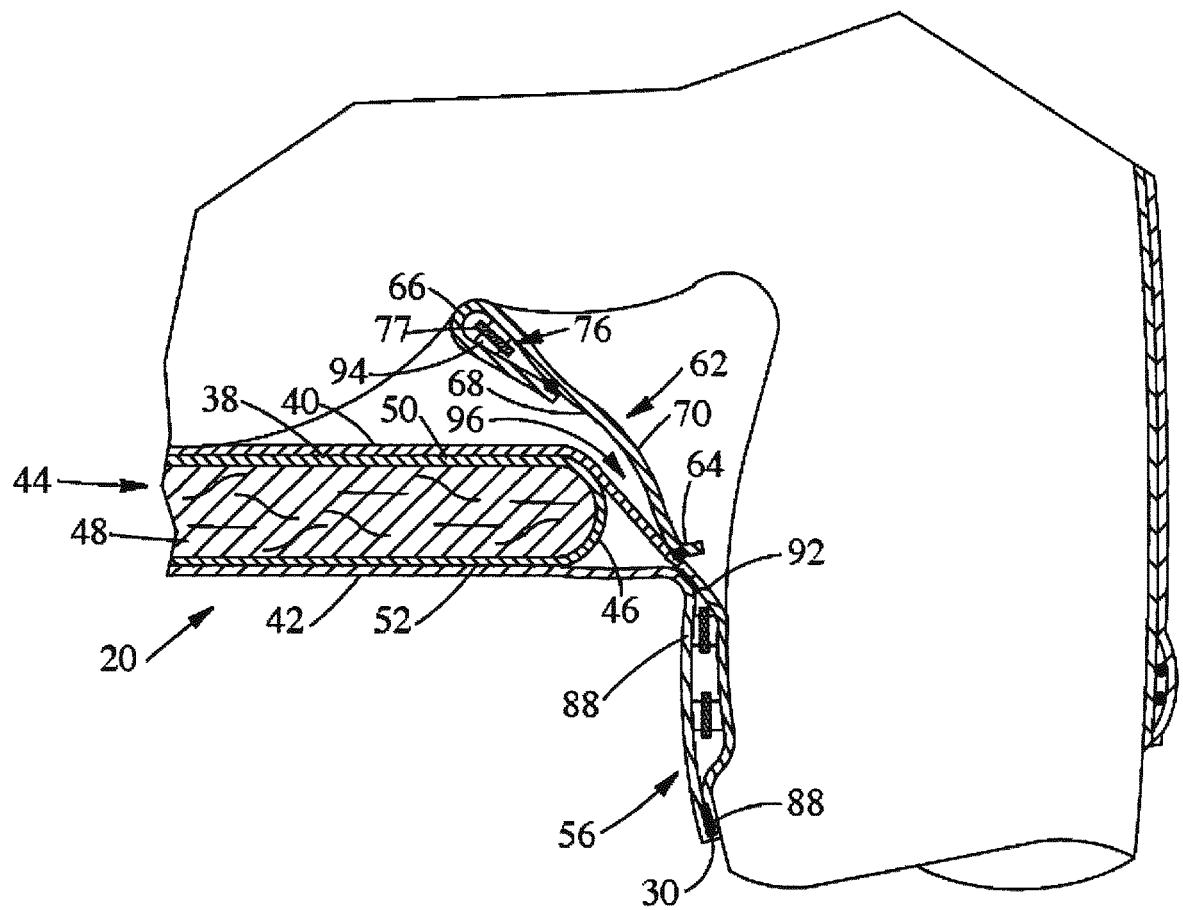
FIG. 5 is a fragmentary coronal view showing the absorbent article of FIG. 1 in place on a wearer.

FIG. 5 is a fragmentary coronal view showing a section of the diaper 20 of FIG. 1 in place on a wearer. A coronal view is a frontal plane that passes through the long axis of the body. As shown in FIG. 5, the gasketing cuffs 56 ride down on the legs and encircle the thighs of the wearer. The barrier cuffs 62 ride up on the legs and run through the crotch region and diverge upwardly over both the buttocks of the wearer. The distal edges 66 are spaced away from the topsheet top surface 40 and lie against the perineum of the wearer. The barrier cuffs 62 are, therefore, pushed snugly against the perineum of the wearer in the crotch region 26 of the diaper 20. The size of the channel 96 is enhanced by the resiliency of the absorbent core 44 because the core tends to push itself away from the perineum. This results in the diaper 20 having channels 96 extending along the crotch region of the wearer. Therefore, body exudates are restrained from penetrating beyond the barrier cuffs 62 because the channels 96 form a barrier to the flow of exudates. As loose fecal material is discharged onto the topsheet 38, the material flows or floats along the topsheet top surface 40 (hereinafter referred to as "surface material"). The surface material moves from the point of discharge toward the longitudinal edges 30 and will contact the barrier cuffs 62 along the inboard surfaces 68. In normal use, gravitational forces will tend to cause the surface material to collect in the channel 96 formed by the standing barrier cuff 62; the material being held in the channels 96 until the diaper 20 can be removed. Containment is achieved because the surface material would have to flow up the channel 96, which direction is substantially directly against the force of gravity when the wearer is in an upright position, in order to penetrate and flow over the distal edges 66 of the barrier cuffs 62. However, should such material flow beyond the barrier cuffs 62, it is retarded from leaking out of the diaper 20 by the gasketing effect achieved by the gasketing cuffs 56, as they draw and gather the side flaps 58 about the legs of the wearer, thereby providing a second and independent effective barrier against leakage.

While barrier cuffs provide additional protection against leakage of floating exudates, it has been found that they may promote diaper sag, particularly in the front waist. A contradiction between leakage protection and sustained fit in the prior art barrier cuffs has been identified. More specifically, and focusing on the front waist region, for improved leakage protection it is desirable that the front bond region 80 have a shorter length (such as 0 to 60 mm), while for prevention of waist sag it is desirable that the front bond region 80 be longer (such as 80 to 110 mm). In identifying this trade-off, applicants have noted that the contractible forces from typical elasticized barrier cuffs are typically approximately 0.3 to 1.0 N, while the forces from a loaded absorbent core may be approximately 1.5 to 3 N. Due to the points at which these forces are applied, however, applicants have found that the smaller forces applied by the unloaded elasticized cuff are a cause of diaper sag. Without wishing to be bound by theory, it is believed that front waist diaper sag will not occur if the following "no sag" criterium is met:

$$f_{pull} \leq \frac{f(c) \cdot w \cdot T \cdot (c_{fr} \cdot \cos\alpha + \sin\alpha)}{r}$$

where, $f_{pull}$ is the force pulling a portion of the diaper defined as the "tension band" down (measured in cN), f(c) is a dimensionless function of c, monotonic increasing, it is small for c=0, c is an anchoring point parameter that indicates where pulling force is applied, T is the tension in the diaper "tension band" (measured in cN), w is the width of the diaper "tension band" (measured in cm), r is the radius of curvature along the band plane (measured in cm), $c_{fr}$ is the diaper material coefficient of friction, and α is the cone angle (measured in degrees).

Figure 6:
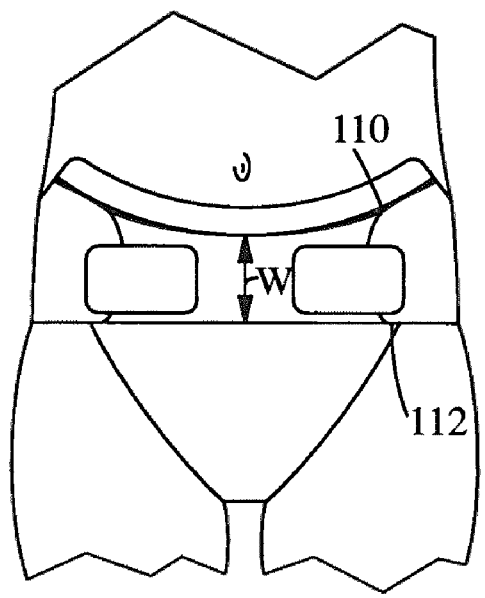
FIG. 6 is a front schematic view of a diaper as worn by a wearer.
Figure 7:
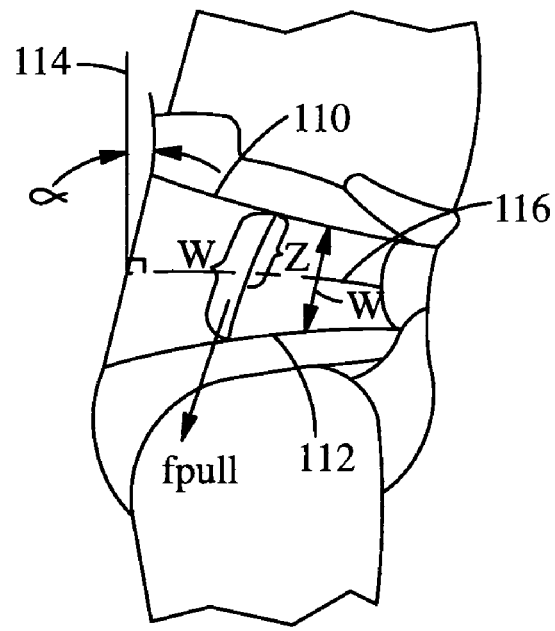
FIG. 7 is a side schematic view of a diaper as worn by a wearer.
Figure 8:
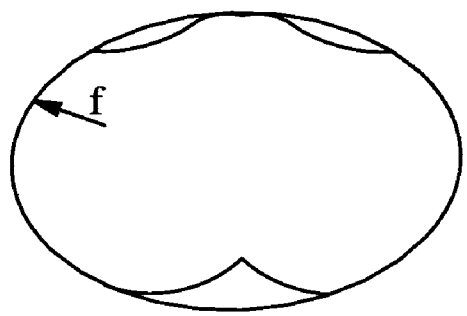
FIG. 8 is a plan view, in cross-section, of a diaper as worn by a wearer.

FIGS. 6-8 illustrate the variables included in the no sag criterium. More specifically, FIG. 6 is a front view of a diaper on a wearer in which the tension band of the diaper is bounded by an upper edge 110 and a lower edge 112, which generally defines the area of the diaper placed in tension to maintain the diaper on the wearer. The width w of the tension band is also illustrated in FIGS. 6 and 7. The anchoring parameter variable c is related to the ratio of dimension Z measured from the upper edge 110 to the point at which the pulling force is applied to the width w of the tension band at the pulling force location (i.e., c=Z/w). The cone angle α is illustrated in FIG. 7 and is measured as the angle of the diaper with respect to a reference line 114 extending normal to the plane of a centerline 116 of the tension band and a line tangential to babies surface. The radius of curvature r is the curvature of the tension band at the anchoring point, as illustrated in FIG. 8.

The relationships identified in the no sag criterium suggest several alternatives for reducing sagging. As used herein, the terms "waist sag" and "waist sagging" refer to the relative movement of the lateral edge 32 of the front waist region 22 versus an anatomic reference, such as a wearer's navel, between the time of initial application of the absorbent article on the wearer and some later time. For example, sagging is less likely if the anchoring parameter c is large, which may be accomplished by locating the anchoring point at the lower edge or below the tension band. Sagging is also less likely if the radius of curvature r is small, which is accomplished by locating the anchoring point where the radius of curvature is small, such as at the hips. The criterium further suggests that a large cone angle α will make sagging less likely, and may be accomplished by locating the anchoring point where the cone angle is large, such as at the hips. Maximizing the tension band width w may be accomplished with greater longitudinal dimension tapes. The relationship of the variables may also suggest reducing sagging by locating the upper edge of the tension band higher relative to the tackdown point (i.e., inner bond edge 83) of the barrier cuff 62. Also, locating the ears of the diaper high on the product (even above the waist) creates a higher landing zone which may increase the likelihood of satisfying the no sag criterium.

In view of the foregoing, applicants have found that a longer front bond region 80 such as through use of intermediate bond 120 in conjunction with bond 78 (or a continuous bond such as those illustrated by FIGS. 1A and 1B) applied to each barrier cuff 62 may reduce front waist sagging while allowing the barrier cuff 62 to effectively retain floating exudates. In some embodiments a length $L_1$ of front bond region 80 may be about ¼ of the longitudinal length of waist region 22 or more, such as ⅓ of the longitudinal length of waist region 22 or more, such as ½ of the longitudinal length of waist region 22 or more. In some embodiments, front bond region 80 may have an $L_1$ of 60 mm or greater, such as 70 mm or greater. In some embodiments, $L_1$ may be between about 80 mm and 110 mm.

As illustrated in FIG. 1, the intermediate bond 120 joins the barrier cuff inboard surface 68 to an interior surface, such as the topsheet top surface 40. The intermediate bond 120 is preferably laterally offset from the bond region 78 so that it is located laterally between the proximal and distal edges 64, 66 of the barrier cuff 62. In the illustrated embodiment, the intermediate bond 120 is located approximately midway between the proximal and distal edges 64, 66. The intermediate bond 120 is further preferably longitudinally offset from the bond 78 so that it is located longitudinally between bond 78 and the lateral axis 34 of the diaper 20. Preferably, the intermediate bond 120 is located within the front waist region 22, however, the intermediate bond 120 may be located in the back waist region 24.

In addition to the considerations identified by the no sag criterium, applicants have identified further considerations for minimizing waist sag. For example, it is believed that lengths of the bond regions, particularly front bond region 80 and panel joint region 155 and locations of their respective inner end bond edge 83 and inner joint edge 149 may affect sagging, particularly in embodiments employing elastically stretchable side panels 154, for example, where the side panel exhibits 100 percent extension under a tensile force of preferably less than about 1000 g/25 mm, such as less than about 750 g/25 mm, such as less than 500 g/25 mm. This is because elastically stretchable side panels 154 can provide a relatively well-defined tension band about the waist of the wearer as opposed to absorbent article embodiments not employing side panels or elastically stretchable side panels which typically have relatively diffused tension about the waist of the wearer. In particular, in embodiments employing elastically stretchable side panels 154 it may be preferable to locate the inner bond edge 81 of the front bond region 80 nearer to or even inner of (i.e., nearer the lateral axis 34) the inner panel joint edge 149.

Figure 9:
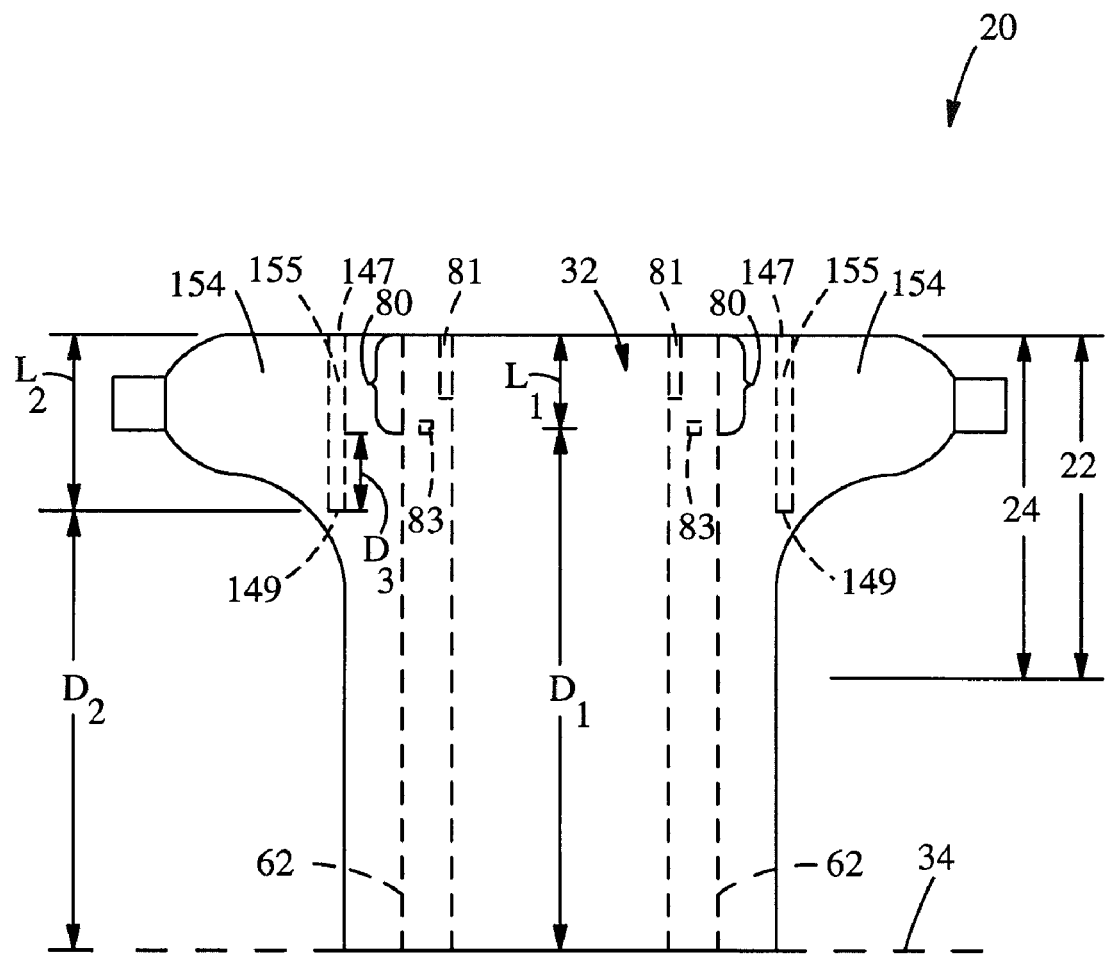
FIG. 9 is a diagrammatic view of the absorbent article of FIG. 1 folded about its lateral axis.

FIG. 9 shows a simplified, diagrammatic view of the diaper 20 in its uncontracted state, folded about the lateral axis 34 and including the elastically stretchable side panels 154 joined at the back waist region 24 at panel joint regions 155. In this embodiment, it may be desirable to locate the inner bond edge 83 of the front bond region 80 nearer to or even inner of (i.e., nearer the lateral axis 34) the inner panel joint edge 149 at the back waist region 24 with the diaper 20 folded about the lateral axis as shown by FIG. 9.

Panel joint region 155 extends from outer panel joint edge 147 to inner panel joint edge 149 a length $L_2$. In some embodiments, $L_2$ is no more than about 2 times the length $L_1$ of bond region 80, such as no more than about equal to $L_1$, such as no more than about ¾ of $L_1$, such as no more than about ½ of $L_1$, such as no more than ⅓ of $L_1$, such as no more than ¼ of $L_1$. In certain embodiments, $L_2$ is between about 1.5 and about ¼ of $L_i$. As can be seen by FIG. 9, outer panel joint edge 147 and outer bond edge 81 are located at respective end edges 32 and the respective regions 155 and 80 extend therefrom, however, the outer panel joint edge 147 and/or outer bond edge 81 may be spaced longitudinally from the respective end edges 32.

Inner panel joint edge 149 is located a longitudinal distance $D_2$ from lateral axis 34 and inner bond edge 83 is located a longitudinal distance $D_1$ from lateral axis 34. While $D_2$ is illustrated as being shorter than $D_1$, $D_2$ may be longer than $D_1$. In some embodiments, $D_2$ is about ½ of $D_1$ or more, such as about ¾ $D_1$ or more, such as at least about equal to $D_1$, such as about 1.5 times $D_1$ or more, such as about 2 times $D_1$ or more. In some embodiments, $D_2$ is between about ½ and about 2 times $D_1$.

In some instances, it may be desirable for inner bond edge 83 to be located nearer the lateral axis 34 than inner panel joint edge 149. In some implementations, however, such as that shown by FIG. 9, inner bond edge 83 is located farther from lateral axis 34 than inner panel joint edge 149. In embodiments where the inner bond edge 83 is located farther from the lateral axis 34 than inner panel joint edge 149, it may be preferable for the inner bond edge 83 to be located a longitudinal distance $D_3$ of no more than about 30 mm (e.g., no more than about 20 mm, no more than about 10 mm, between about 1 mm and about 30 mm) from the inner panel joint edge 149.

Figure 10:
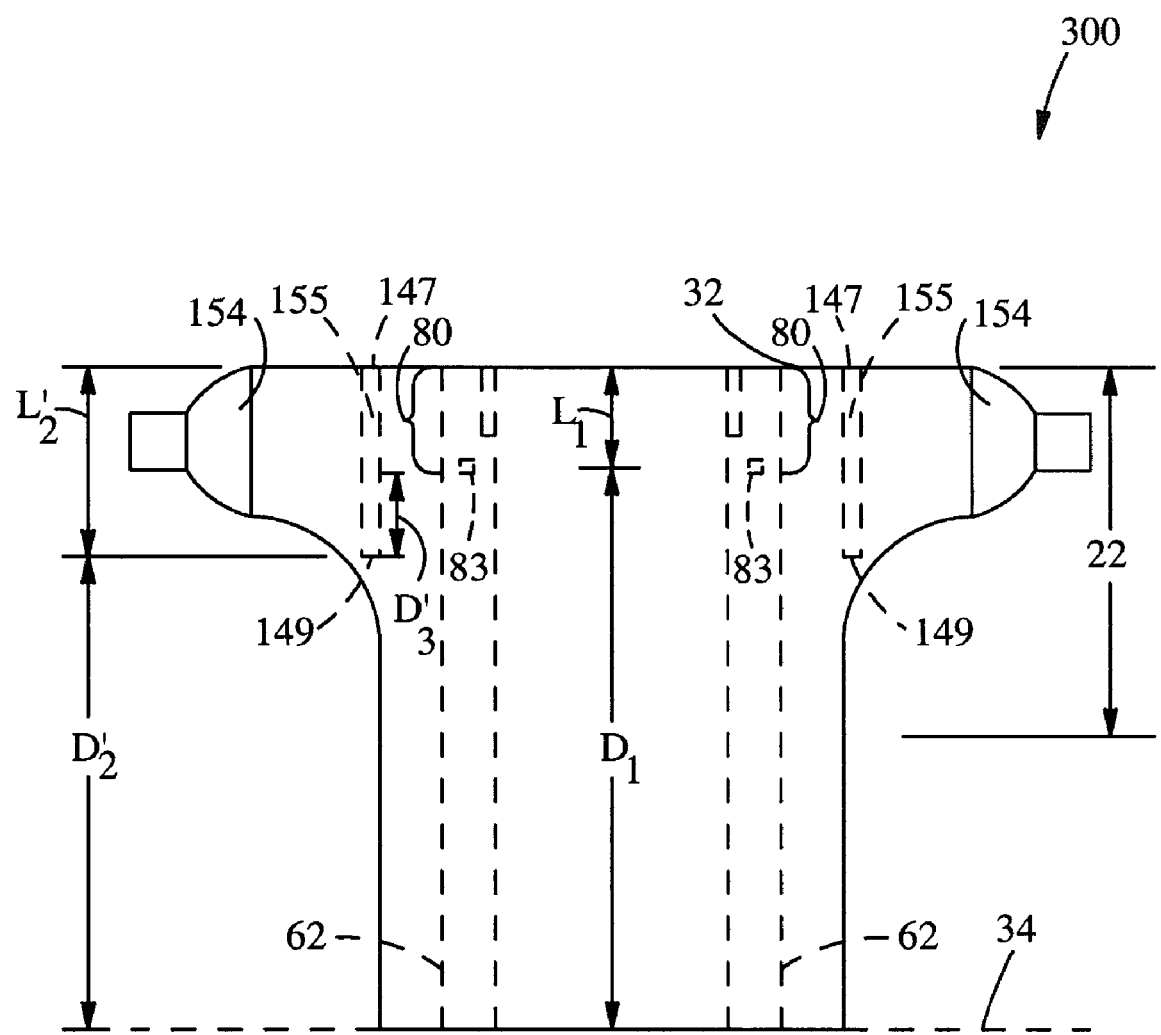
FIG. 10 is a sectional, plan view of another embodiment of an absorbent article.

FIG. 10 shows a partial view of a front waist region 22 of a another diaper 300 embodiment including elastically stretchable side panels 154 joined at the front waist region 22. As described above, side panels 154 are joined to the chassis (e.g., at backsheet 42) at panel joint regions 155. Panel joint region 155 extends from outer panel joint edge 147 to inner panel joint edge 149 a length $L_2'$. In some embodiments, $L_2'$ is no more than about 2 times the length $L_1$ of bond region 80, such as no more than about equal to $L_1$, such as no more than about ¾ of $L_1$, such as no more than about ½ of $L_1$, such as no more than ⅓ of $L_1$, such as no more than ¼ of $L_1$. In certain embodiments, $L_2$ is between about 1.5 and about ¼ of $L_1$. As can be seen by FIG. 10, outer panel joint edge 147 and outer bond edge 81 are located at end edge 32 and the respective regions 155 and 80 extend therefrom, however, the outer panel joint edge 147 and/or outer bond edge 81 may be spaced longitudinally from the end edge 32.

Inner panel joint edge 149 is located a longitudinal distance $D_2{}'$ from lateral axis 34 and inner bond edge 83 is located a longitudinal distance $D_1$ from lateral axis 34. While $D_2{}'$ is illustrated as being shorter than $D_1$, $D_2{}'$ may be longer than $D_1$. In some embodiments, $D_2{}'$ is about ½ of $D_1$ or more, such as about ¾ $D_1$ or more, such as at least about equal to $D_1$, such as about 1.5 times $D_1$ or more, such as about 2 times $D_1$ or more. In some embodiments, $D_2{}'$ is between about ½ and about 2 times $D_1$.

In some instances, it may be desirable for inner bond edge 83 to be located nearer the lateral axis 34 than inner panel joint edge 149. In some implementations, however, such as that shown by FIG. 10, inner bond edge 83 is located farther from lateral axis 34 than inner panel joint edge 149. In embodiments where the inner bond edge 83 is located farther from the lateral axis than inner panel joint edge 149, it may be preferable for the inner bond edge 83 to be located a longitudinal distance $D_3{}'$ of no more than about 30 mm (e.g., no more than about 20 mm, no more than about 10 mm, between about 1 mm and about 30 mm) from the inner panel bond edge 149.

Lowering the tackdown point of the barrier cuff 62 may also allow for use of flexible and profiled absorbent cores. Use of flexible and profiled absorbent cores in conjunction with a lower tackdown point of the barrier leg cuff is described in greater detail in U.S. patent application Ser. No. 11/251,311, entitled "Absorbent Article Including Barrier Leg Cuff Structure and Absorbent Core with Superabsorbent Material," filed on the same day as the instant application.

Figure 11:
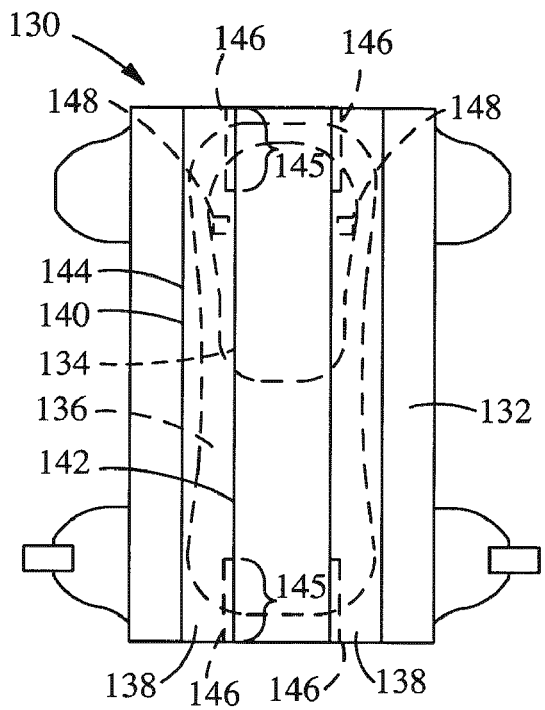
FIG. 11 is a plan view of an alternative embodiment of an absorbent article.

Anchoring the barrier cuff to a diaper element having greater stiffness, such as the absorbent core 44, or a fastener component landing zone may also reduce sag. Referring to FIG. 11, a diaper 130 is illustrated having a topsheet 132, acquisition layer 134, absorbent core 136, and backsheet (not shown). Two barrier cuffs 138 are joined to the topsheet 132 and include a proximal edge 140 and a distal edge 142. Each proximal edge 140 is attached to the topsheet 132 at an edge bond 144 running along substantially the entire length of the barrier cuff. The distal edges 142 are attached to the topsheet 132 at end bonds regions 145 including end bonds 146 located at opposed ends of the distal edges 142 and intermediate bonds 148 located at points laterally and longitudinally offset from the end bonds 146 yet at locations which allow attachment to either or both of the acquisition layer 134 and the absorbent core 136. The end bonds 146 and intermediate bonds 148 define inner and outer edges of end bond regions 145. By anchoring the barrier cuffs 138 to the stiffer diaper elements, diaper sag in the front waist region is reduced.

Figure 12:
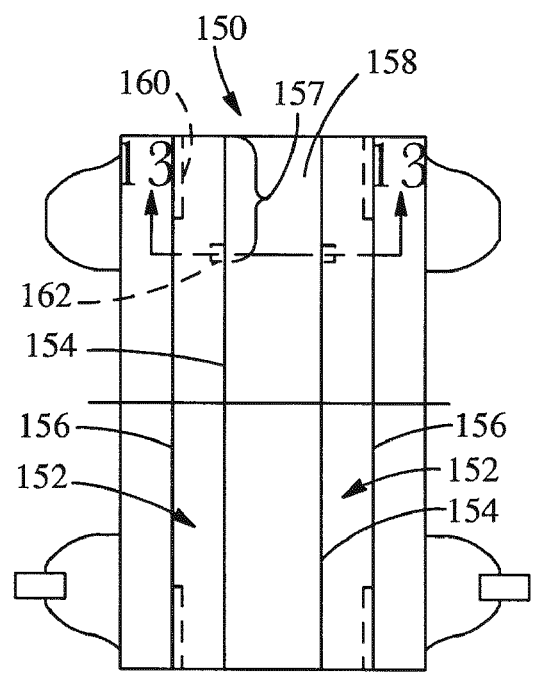
FIG. 12 is a plan view of yet another alternative embodiment of an absorbent article.
Figure 13:
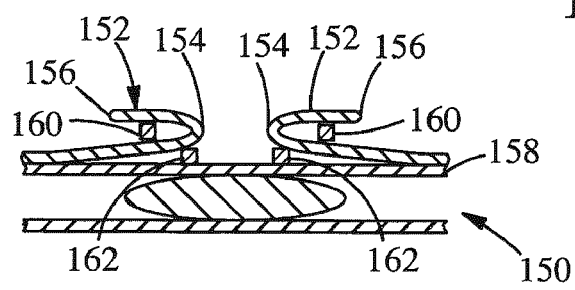
FIG. 13 is a cross-sectional view taken along section line 13-13 of FIG. 12.

While the previous embodiments illustrate barrier cuffs having a distal edge located nearer the longitudinal centerline, an intermediate bond is also effective for diapers having back-folded barrier cuffs where the distal edge is located farther from the longitudinal centerline. Referring to FIGS. 12 and 13, a diaper 150 includes barrier cuffs 152 having proximal edges 154 and distal edges 156. The distal edges 156 are anchored at end bond regions 157 defined by end bonds 160 and intermediate bonds 162. Intermediate bonds 162 are located laterally and longitudinally offset from the end bonds 160 and along with the end bonds 160 form inner and outer edges of end bond regions 157. In the illustrated embodiment, the intermediate bonds 162 are aligned with the proximal edges 154 of the barrier cuffs 152 to minimize sagging in the front waist region.

Figure 14:
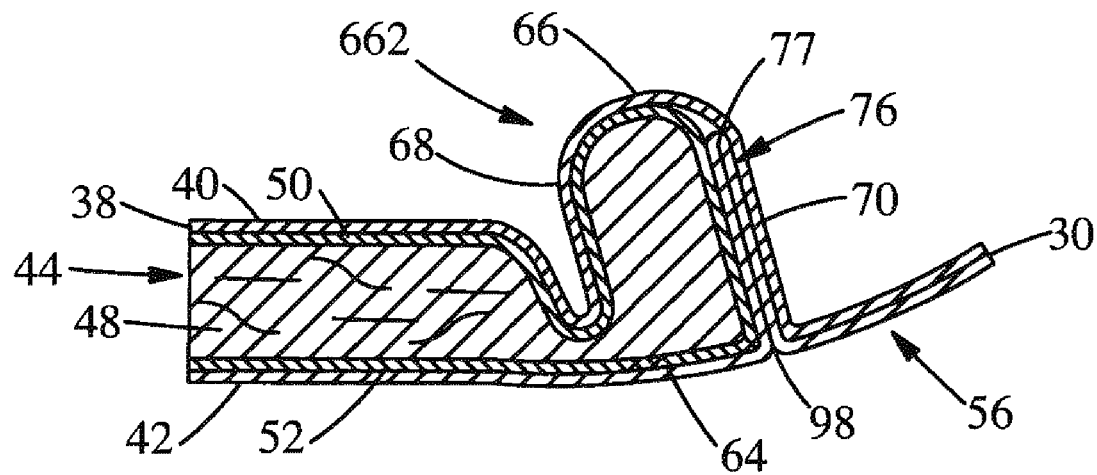
FIG. 14 is a fragmentary sectional view of an alternative embodiment of a barrier cuff assembly.

FIG. 14 illustrates a sectional view of an alternative barrier cuff 662 formed by pleating the entire diaper structure (i.e., the backsheet 42, the absorbent core 44, and the topsheet 38). After pleating the structure, the proximal edges 64 of the barrier cuff 662 are secured together by adhesive 98. The barrier cuff 662 may have spacing means such as spacing elastic members 77 secured within the barrier cuff 662 so elasticize the distal edges 66 so as to space the distal edges 66 away from the top surface 40 of the topsheet 38.

Figure 15:
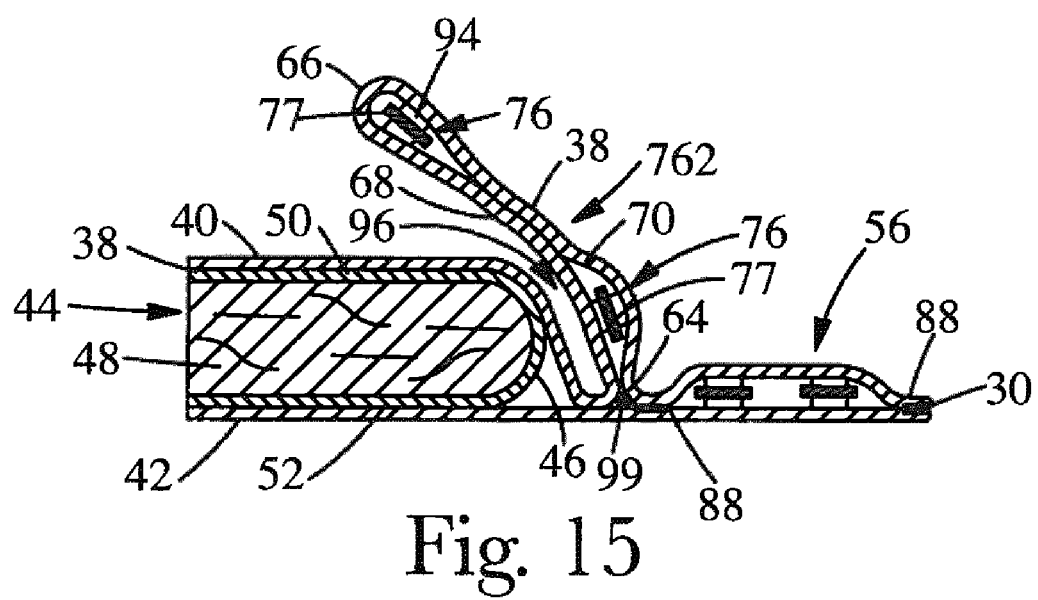
FIG. 15 is a fragmentary sectional view of a further alternative embodiment of a barrier cuff assembly.

FIG. 15 illustrates a further barrier cuff arrangement. A unitary barrier cuff 762 is formed by U-folding or pleating the topsheet of the diaper 20. The topsheet is folded upon itself to form a distal edge 66; spacing elastic members 77 are secured within the tunnel formed in the distal edge 66. The proximal edge 64 is secured by adhesive attachment means 99 such as a glue bead made of hot melt adhesive.

Figure 17:
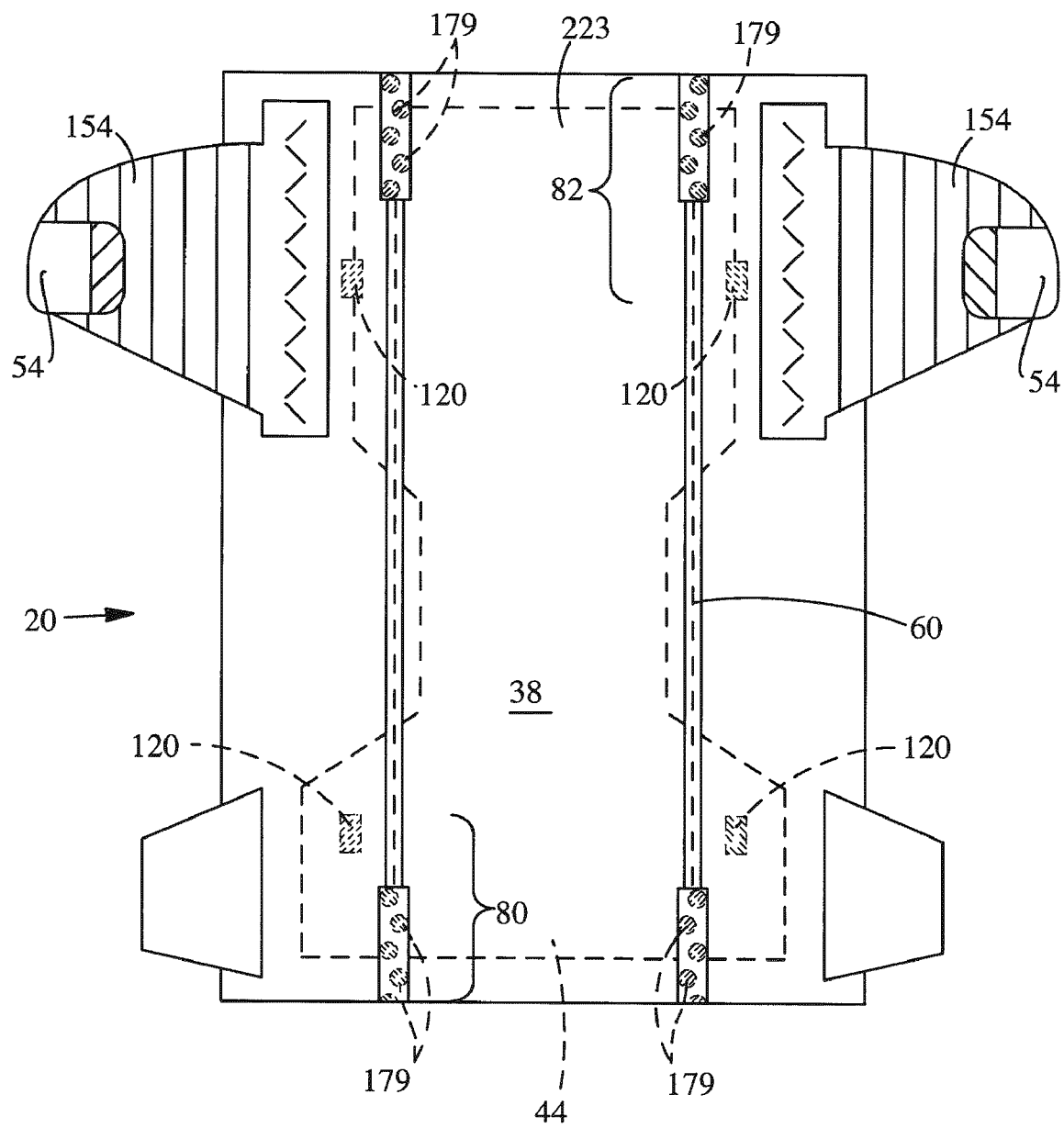
FIG. 17 is a plan view of another alternative embodiment of an absorbent article.

FIG. 17 illustrates an end bond region 80, 82 comprising a series of discrete patterned bonds 179 such as pressure bonds for use on a barrier cuff such as, for example, one of the barrier cuffs described herein. The intermediate bond 120 in such an embodiment is discrete from and not part of the general pattern formed by the patterned bonds 179 in the end bond region 80, 82.

Figure 16:
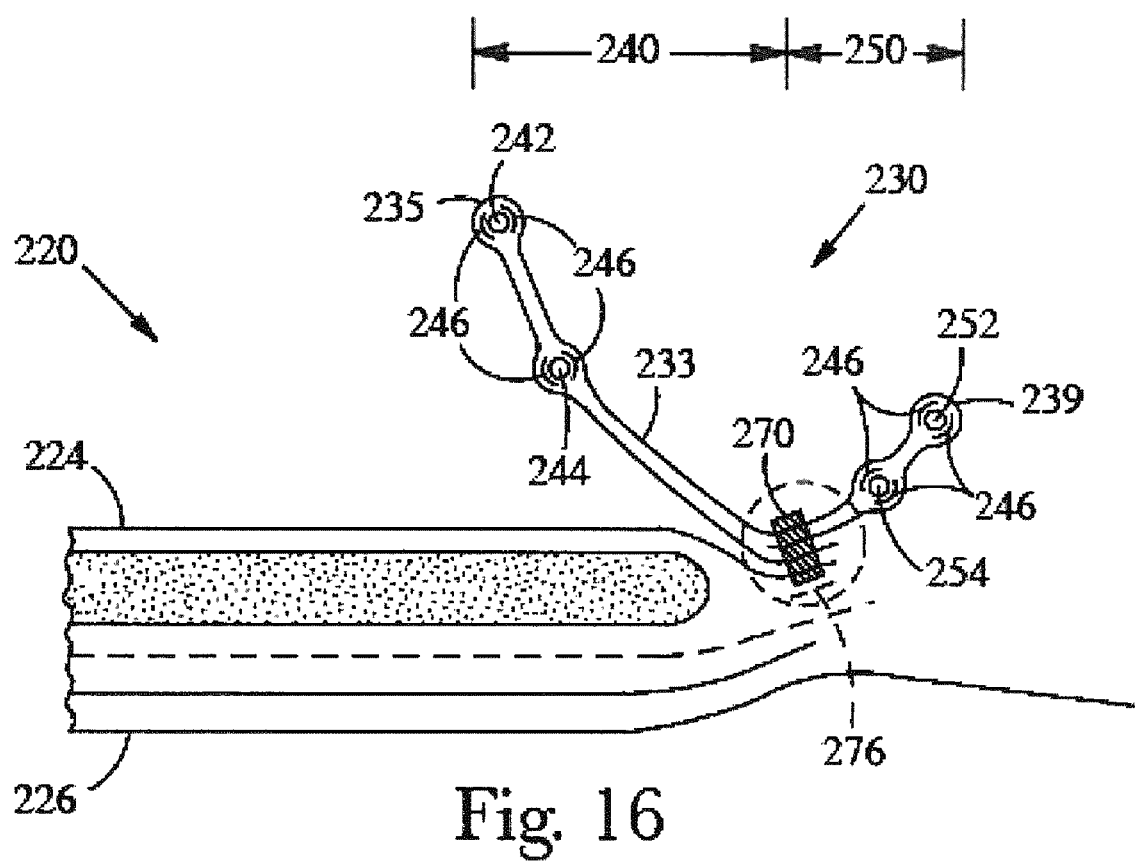
FIG. 16 is a fragmentary sectional view of a diaper embodiment having a dual cuff barrier cuff.

In addition to single cuff barrier cuffs, the elongated end bond region such as any of those described above may further be applied to dual cuff barrier cuffs. FIG. 16 illustrates one embodiment of a dual cuff barrier cuff 230 in fragmentary sectional view taken in a crotch region of a diaper 220 as it is shaped before being applied to the wearer (i.e., the diaper is subjected to elastic contraction). Dual cuff 230 has a proximate end at bond 270, distal ends 239 and 235 and regions therebetween identified as first cuff 240 and second cuff 250. Dual cuff 230 may be constructed from a continuous cuff material 233 that substantially envelopes the elastics of first cuff 240 and second cuff 250. More specifically, first cuff 240 has at least one elastic (although two elastics 242, 244 are shown) and second cuff 250 also has at least one elastic (although two elastics 252, 254 are shown) that are enveloped within cuff material 233. In this way, only a continuous cuff material 233 is used and manipulated during the construction of dual cuff 230, thus making easier the manufacturing of said dual cuff. Moreover, cuff material 233 need only be enclosed/bonded at a single location, as exampled by cuff bond 270, in order to substantially envelope elastics 242, 244, 252, 254, thus providing improved barrier properties by minimizing the number of potential leakable locations (e.g., bonding locations). Herein, "continuous cuff material" means a cuff material that is continuous along a path beginning from the cuff end bond, along said cuff material, and ending at the same cuff end bond such that the dual cuff 230 is substantially constructed of two layers of the materials, whether it is the same or different materials. For example, the continuous cuff material 233 may be constructed of a lesser-water-permeable material (e.g., spunbound material which is inexpensive) with a more-water-permeable material (e.g., meltblown material which is more expensive) placed inside said lesser-water-permeable material. In another example, cuff material 233 may be constructed of a spunbound-meltblown laminate. In yet another example, cuff material 233 may be constructed of a series of various materials so long as they are continuous. In yet another example, cuff material 233 may be treated to increase its hydrophobicity. Such hydrophobic treatments include, but are not limited to, the application of hydrophobic surface coating (as exampled in co-pending U.S. patent application Ser. No. 60/543,785, entitled "Hydrophobic Surface Coated Absorbent Articles And Associated Methods", filed on Feb. 11, 2004) and flouro-treatment (as exampled in co-pending U.S. patent application No. 2004/0092902, entitled "Disposable Absorbent Articles With Masking Topsheet", Published on May 13, 2004). In yet another example, it may be desirable that dual cuff 230 be connected to diaper 220 by way of a single bond (e.g., adhesive, ultrasonic; e.g., cuff bond 270 to topsheet 224).

Cuff bond 270 may extend substantially the entire longitudinal length of diaper 220. Cuff bond 270 may be adhesive, ultrasonic bonding, compression bonding, thermal bonding, combinations thereof, and any other suitable bonding means known in the art which is appropriate for the specific materials employed. Cuff bond 270 may also join dual cuff 230 to topsheet 224. Lastly, an adhesive 276 having liquid impermeability properties may be applied between the topsheet 224 and backsheet 226 (or more specifically shown herein, backsheet inner layer 227) to provide improved barrier properties. Adhesive 276 may be located juxtaposed to intermediate bond 270; however, so long as adhesive 276 helps to provide a containment of exudates, then its actual location may be variable. Further, it may be desirable for the cuff material to only be bonded to itself by the cuff bond (i.e., no other bond similar to cuff bond 270 is used). Lastly, it may be desirable for both first cuff 240 and second cuff 250 to be barrier cuffs.

Elastics 242, 244, 252, 254 may be operatively associated with their respective cuff by securing it within said cuff with an elastic attachment element 246. The elastic attachment element 246 should be flexible and of sufficient adhesiveness to hold elastics 242, 244, 252, 254 in their stretched condition. Elastics 242, 244, 252, 254, having a first and second end, may be secured to their respective cuff only near their ends or along their entire length. Elastic attachment element 246 may be glue beads made of hot melt adhesive such as marketed by Findley Adhesives Incorporated, Elmgrove, Wis., as Findley Adhesives 581. Alternatively, elastic attachment element 246 may take the form of an ultrasonic bond or heat/pressure seal. A more detailed description of the manner in which the elastic attachment element 246 may be positioned and secured to their respective cuff can be found in U.S. Pat. No. 4,081,301, issued to Buell on Mar. 28, 1978, and in U.S. Pat. No. 4,253,461, issued to Strickland and Visscher on Mar. 3, 1981, both of which are incorporated herein by reference. While elastics 242, 244 in first cuff 240 and elastics 252, 254 in second cuff 250 were shown, it would be obvious to those skilled in the art that one or more elastics may be used in each cuff without departing from the spirit and scope of the invention.

Elastics 242, 244, 252, 254 which have been found suitable are elastic strands having a cross section of 0.18 mm by 1.5 mm and made from natural rubber as available from Easthampton Rubber Company of Stewart, Va., under the trademark L-1900 Rubber Compound. Other suitable elastics can be made from natural rubber, such as elastic tape sold under the trademark Fulflex 9411 by Fulflex Company of Middletown, R. I. Elastic strands sold as Fullflex may have a cross section of about 0.18 mm by 0.52 mm and be suitable. Elastics 242, 244, 252, 254 may also comprise any heat shrinkable elastic material as is well known in the art. Other suitable elastic materials may comprise a wide variety of materials as are well known in the art include elastomeric films, polyurethane films, elastomeric foams, formed elastic scrim and synthetic elastomers (e.g., LYCRA). In addition, elastics 242, 244, 252, 254 may take a multitude of configurations. For example, the width may be varied; a single strand or several parallel or non-parallel strands of elastic material may be used; or a variety of shaped may be used including rectilinear and curvilinear.

The dual cuff barrier cuff embodiments may also include pockets for receiving and containing waste, spacers which provide voids for waste, barriers for limiting the movement of waste in the article, compartments or voids which accept and contain waste materials deposited in the diaper 220, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT application No. WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,062,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000.

Figure 18:
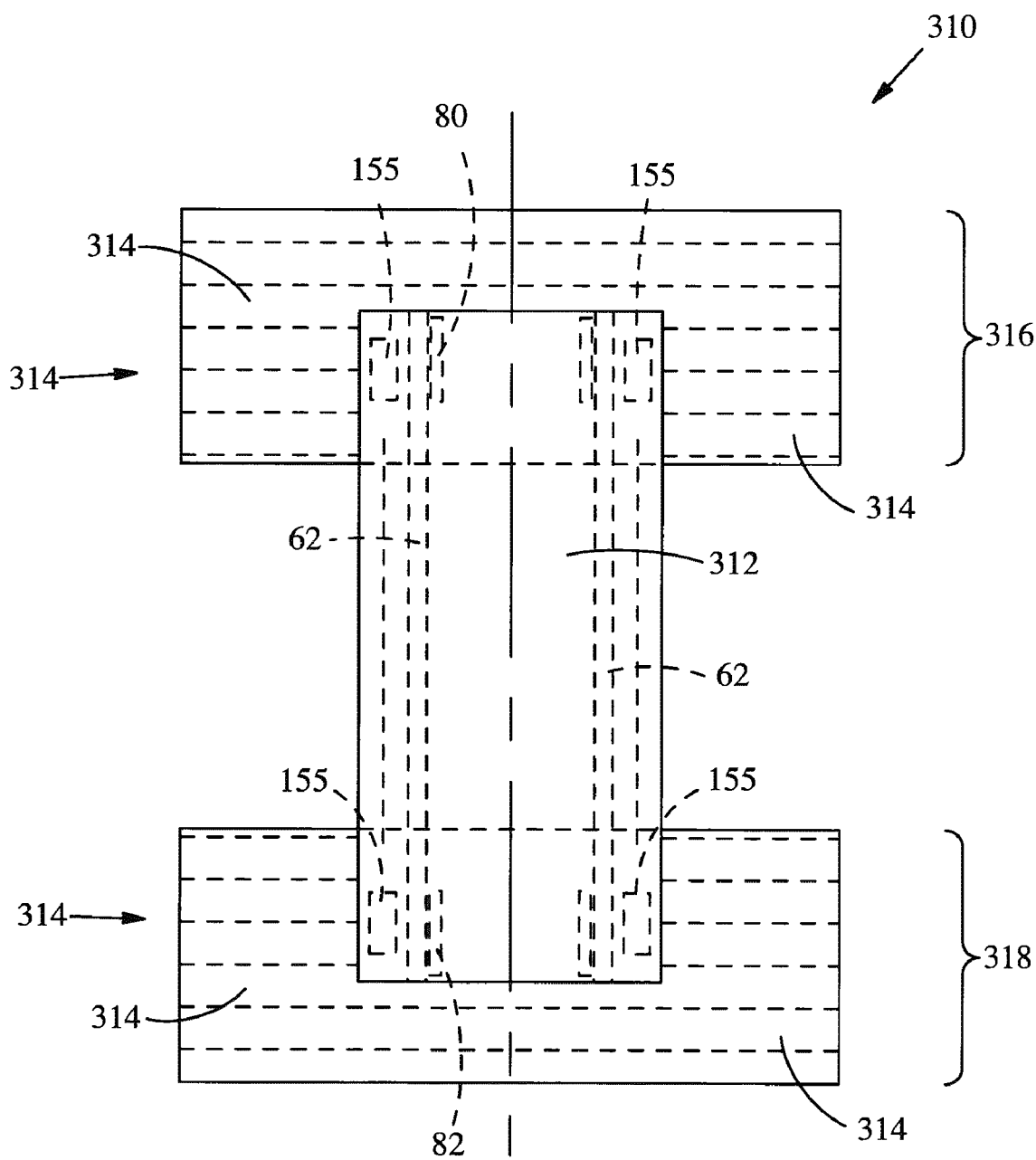
FIG. 18 is a plan view of another alternative embodiment of an absorbent article.

Referring now to FIG. 18, various diaper constructions may include other elastically extensible structures that form elastically stretchable side panels. For example, FIG. 18 shows a diaper 310 that includes a main body or chassis 312 and a belt structure 314 that forms elastically stretchable side panels 314 that extend laterally from the chassis 312 in front waist region 316 and back waist region 318. The belt structure 314 may be joined to the chassis 312 at one or more joint region 155 that extends a longitudinal length of the diaper 310. The diaper 310 also includes barrier leg cuffs 62 that include bond regions 80, 82 similar to those described above. Details of diaper 310 are described in WO 2005051263 entitled "Disposable Pull-On Garment."

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a chassis including a topsheet and a backsheet joined to the topsheet and an absorbent core located between the topsheet and the backsheet, the chassis having a front waist region, a back waist region, a crotch region located between the front waist region and the back waist region, a front waist edge, a rear waist edge, a longitudinal axis extending through the front and back waist regions and a lateral axis substantially perpendicular to the longitudinal axis, said lateral axis positioned midway between the front waist edge and the rear waist edge in the longitudinal direction;
at least one barrier cuff strip extending in a longitudinal direction from the front waist region to the back waist region along the topsheet, the barrier cuff strip including a front end at the front waist region, a back end at the back waist region and proximal and distal edges connecting the front end and the back end, the barrier cuff strip distal edge being attached to the topsheet at a cuff end bond region having an outer bond edge at one of the front and back ends of the barrier cuff strip and an inner bond edge spaced longitudinally from the outer bond edge; and
a side panel extending laterally beyond a side of the chassis and joined to the chassis at one of the front and back waist regions at a panel joint region extending between an outer panel joint edge and an inner panel joint edge, the side panel comprising an elastically stretchable material;
wherein a longitudinal distance from the lateral axis to the inner panel joint edge is at least about ¼ of a longitudinal distance from the lateral axis to the inner bond edge of the cuff end bond region.

2. The absorbent article of claim 1, wherein the longitudinal distance from the lateral axis to the inner panel joint edge is at least about ½ of the longitudinal distance from the lateral axis to the inner bond edge of the cuff end bond region.

3. The absorbent article of claim 1, wherein the longitudinal distance from the lateral axis to the inner panel joint edge is at least about ¾ of the longitudinal distance from the lateral axis to the inner bond edge of the cuff end bond region.

4. The absorbent article of claim 1, wherein the longitudinal distance from the lateral axis to the inner panel joint edge is at least about equal to the longitudinal distance from the lateral axis to the inner bond edge of the cuff end bond region.

5. The absorbent article of claim 1, wherein the longitudinal distance from the lateral axis to the inner panel joint edge is greater than the longitudinal distance from the lateral axis to the inner bond edge of the cuff end bond region.

6. The absorbent article of claim 1, wherein the inner panel joint edge is spaced longitudinally from the inner bond edge of the cuff bond region a distance of about 30 mm or less.

7. The absorbent article of claim 1, wherein the inner bond edge is longitudinally spaced from the outer bond edge a longitudinal length of about ½ or more of a longitudinal length of the front waist region.

8. The absorbent article of claim 2, wherein the inner bond edge is located in the front waist region.

9. The absorbent article of claim 8, wherein the side panel is joined to the chassis at the back waist region at the panel joint region, the longitudinal distance from the lateral axis to the inner panel joint edge and the longitudinal distance from the lateral axis to the inner bond edge of the cuff end bond region being measured with the absorbent assembly folded at the lateral axis.

10. The absorbent article of claim 8, wherein a bond defining the inner bond edge and the outer bond edge extends continuously from the inner bond edge to the outer bond edge.

11. The absorbent article of claim 8, wherein a first bond defines the outer bond edge and a second bond defines the inner bond edge, the second bond being spaced apart longitudinally from the first bond.

12. The absorbent article of claim 11, wherein the second bond is offset laterally from the first bond.

13. The absorbent article of claim 1, wherein the inner bond edge is longitudinally spaced from the outer bond edge a longitudinal length of about 60 mm or more.

14. The absorbent article of claim 1, wherein the inner bond edge is longitudinally spaced from the outer bond edge a longitudinal length of about 70 mm or more.

15. The absorbent article of claim 13, wherein the inner bond edge being longitudinally spaced from the outer bond edge a longitudinal length of between about 80 mm and 110 mm.

16. The absorbent article of claim 1, wherein the side panel is elastically stretchable in the lateral direction.

17. The absorbent article of claim 16, wherein the side panel is elastically stretchable in the longitudinal direction.

18. The absorbent article of claim 1, wherein the side panel is formed separately from the absorbent assembly and affixed to the absorbent assembly.

19. The absorbent article of claim 1 further comprising a fastener component affixed to the side panel.

20. The absorbent article of claim 1 comprising a pair of side panels extending laterally beyond opposite sides of the absorbent assembly, each side panel comprising the elastically stretchable material.

21. The absorbent article of claim 1, wherein said barrier cuff strip includes a longitudinally extending elastic gathering member attached adjacent to the distal edge such that when allowed to relax, the elastic gathering member contracts and lifts the distal edge away from the topsheet.

22. The absorbent article of claim 1, wherein the side panel exhibits 100 percent extension under a tensile force of less than about 1000 g/25 mm.

23. The absorbent article of claim 1, wherein the side panel exhibits 100 percent extension under a tensile force of less than about 750 g/25 mm.

24. The absorbent article of claim 1, wherein the side panel exhibits 100 percent extension under a tensile force of less than about 500 g/25 mm.

25. An absorbent article comprising:
- a chassis having a front waist region, a back waist region, and a crotch region between the front and back waist regions, a front waist edge, a rear waist edge, an interior surface and an exterior surface, and a longitudinal axis and a lateral axis, said lateral axis positioned midway between the front waist edge and the rear waist edge in the longitudinal direction;
- two laterally opposed, longitudinally extending barrier cuff strips associated with the interior surface of the chassis, each barrier cuff strip having longitudinally opposed front and back ends disposed in the respective waist regions and longitudinally extending proximal and distal edges connecting the front and back ends, each barrier cuff strip distal edge being attached to the interior surface of the chassis at cuff end bond regions that extend from an outer bond edge adjacent to the respective front and back ends of the barrier cuff strip to an inner bond edge; and
- a side panel extending laterally beyond a side of the chassis and joined to the chassis at one of the front and back waist regions at a panel joint region extending between an outer panel joint edge and an inner panel joint edge, the side panel comprising an elastically stretchable material;
- wherein a longitudinal length from the outer bond edge to the inner bond edge of at least one of the cuff bond regions is at least about ½ of a longitudinal length from the outer panel joint edge to the inner panel joint edge of the panel joint region.

* * * * *

UNITED STATES PATENT AND TRADEMARK OFFICE
CERTIFICATE OF CORRECTION

PATENT NO. : 7,918,839 B2  Page 1 of 1
APPLICATION NO. : 11/251421
DATED : April 5, 2011
INVENTOR(S) : Ehrnsperger et al.

It is certified that error appears in the above-identified patent and that said Letters Patent is hereby corrected as shown below:

Column 16

Line 35, delete "$L_i$" and insert --$L_1$--.

Signed and Sealed this
Twenty-first Day of February, 2012

David J. Kappos
*Director of the United States Patent and Trademark Office*